United States Patent
Eun et al.

(10) Patent No.: US 10,143,428 B2
(45) Date of Patent: Dec. 4, 2018

(54) METHOD AND APPARATUS FOR PROVIDING INFORMATION RELATED TO LOCATION OF TARGET OBJECT ON MEDICAL APPARATUS

(71) Applicant: Samsung Electronics Co., Ltd., Suwon (KR)

(72) Inventors: Dong-jin Eun, Bucheon-si (KR); Tae-kyun Kim, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 260 days.

(21) Appl. No.: 14/107,687

(22) Filed: Dec. 16, 2013

(65) Prior Publication Data

US 2015/0003674 A1    Jan. 1, 2015

(30) Foreign Application Priority Data

Jun. 26, 2013    (KR) .................. 10-2013-0073966

(51) Int. Cl.
*G06T 7/00*    (2017.01)
*A61B 6/04*    (2006.01)
(Continued)

(52) U.S. Cl.
CPC .................. *A61B 6/04* (2013.01); *A61B 6/08* (2013.01); *A61B 6/461* (2013.01); *G06T 7/73* (2017.01);
(Continued)

(58) Field of Classification Search
None
See application file for complete search history.

(56) References Cited

U.S. PATENT DOCUMENTS 4,831,645 A * 5/1989 Guenther ............. A61B 5/1077
378/205
5,823,192 A    10/1998 Kalend et al.
(Continued)

FOREIGN PATENT DOCUMENTS

JP    2000350719 A  * 12/2000
JP    2001-259060       9/2001
(Continued)

OTHER PUBLICATIONS

PCT International Search Report and Written Opinion of the International Searching Authority dated Sep. 26, 2014 in corresponding International Patent Application No. PCT/KR2014/005553.

*Primary Examiner* — Vu Le
*Assistant Examiner* — Tracy Mangialaschi
(74) *Attorney, Agent, or Firm* — Staas & Halsey LLP

(57) ABSTRACT

Provided is a method of providing location information regarding a location of a target object through a medical apparatus. The method includes setting photographing conditions about the target object, acquiring current location information of the target object, acquiring recommended location information of the target object according to the photographing conditions, outputting the acquired recommended location information, comparing the current location information with the recommended location information, and outputting additional information about a current location of the target object, according to a comparison result.

23 Claims, 35 Drawing Sheets

(51) Int. Cl.
  *A61B 6/08* (2006.01)
  *A61B 6/00* (2006.01)
  *G06T 7/73* (2017.01)

(52) U.S. Cl.
  CPC .......... *A61B 6/4405* (2013.01); *A61B 6/4464* (2013.01); *G06T 2207/10116* (2013.01); *G06T 2207/30004* (2013.01)

(56) References Cited

U.S. PATENT DOCUMENTS

| | | | |
|---|---|---|---|
| 8,504,136 B1 * | 8/2013 | Sun | A61B 5/1076 600/407 |
| 2002/0023652 A1 * | 2/2002 | Riaziat | A61N 5/1049 128/897 |
| 2002/0065461 A1 * | 5/2002 | Cosman | 600/426 |
| 2003/0225325 A1 * | 12/2003 | Kagermeier et al. | 600/407 |
| 2011/0135190 A1 * | 6/2011 | Maad | A61B 6/0407 382/154 |
| 2011/0207504 A1 | 8/2011 | Anderson et al. | |
| 2011/0305320 A1 | 12/2011 | Suuronen et al. | |
| 2013/0121468 A1 * | 5/2013 | Ohta | A61B 6/4405 378/63 |
| 2014/0348296 A1 * | 11/2014 | Goossen et al. | 378/62 |

FOREIGN PATENT DOCUMENTS

| | | |
|---|---|---|
| JP | 2010-246883 | 11/2010 |
| KR | 10-0707790 | 4/2007 |
| KR | 10-2009-0078646 | 7/2009 |
| KR | 10-2009-0078649 | 7/2009 |
| WO | WO 2013072872 A1 * | 5/2013 |

* cited by examiner

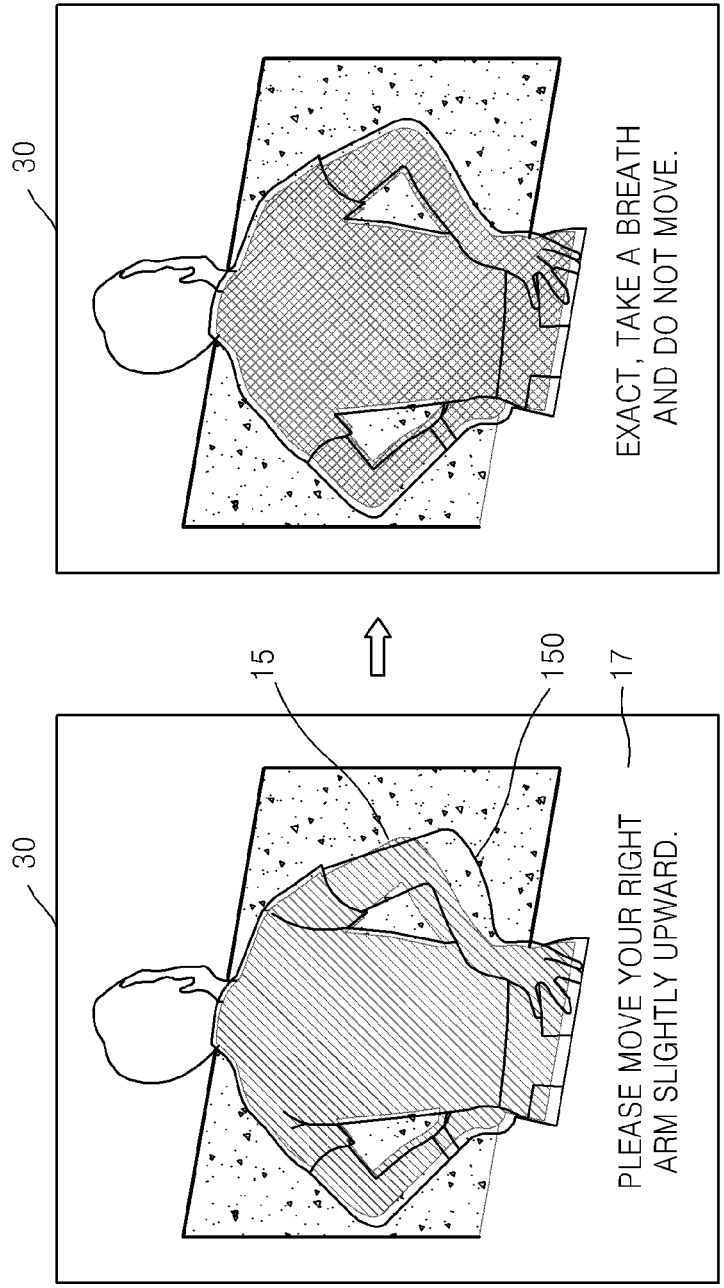

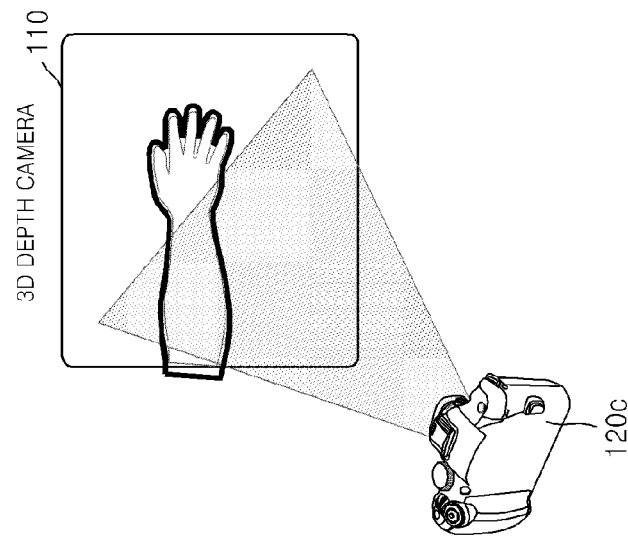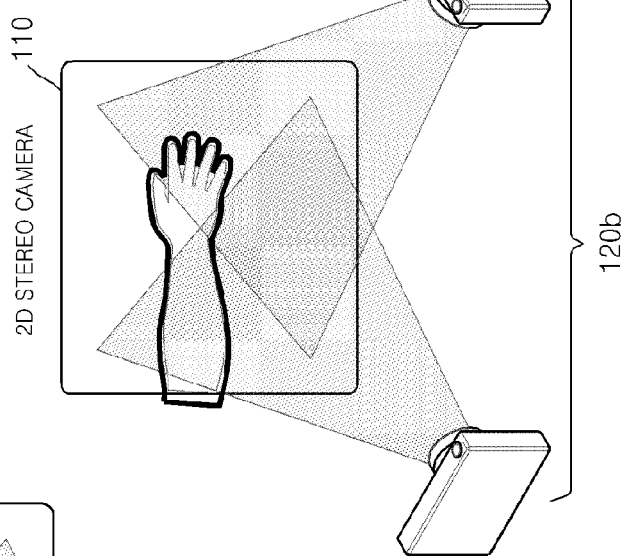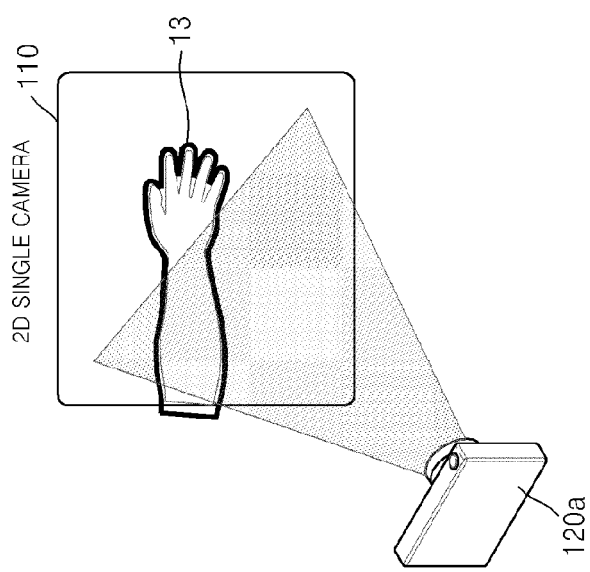

FIG. 7
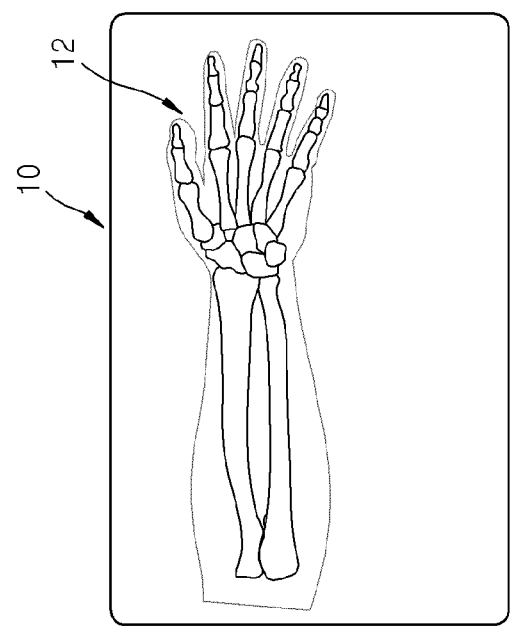
REFERENCE IMAGE
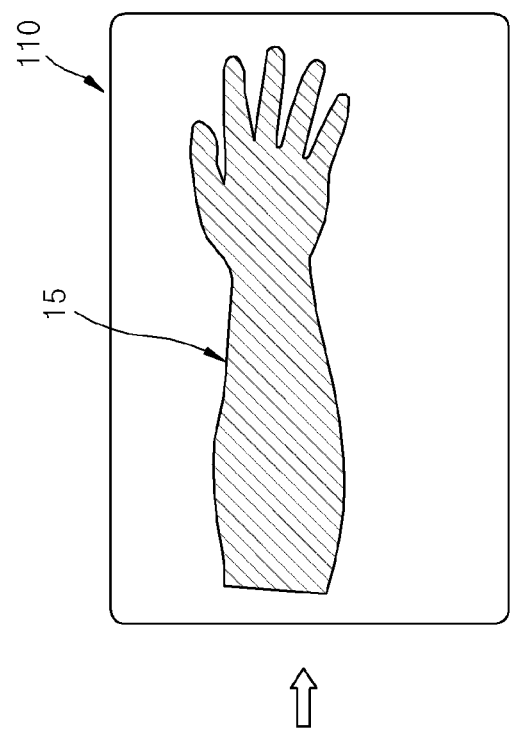

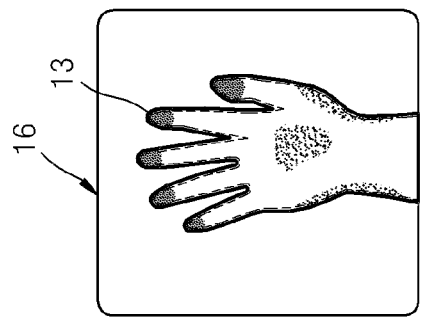
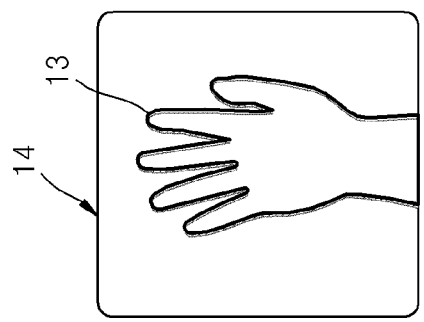
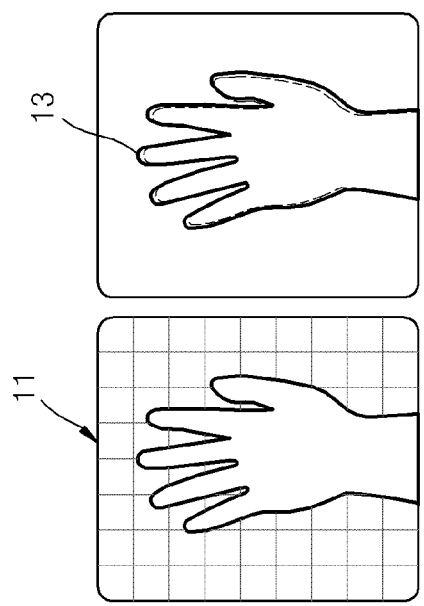

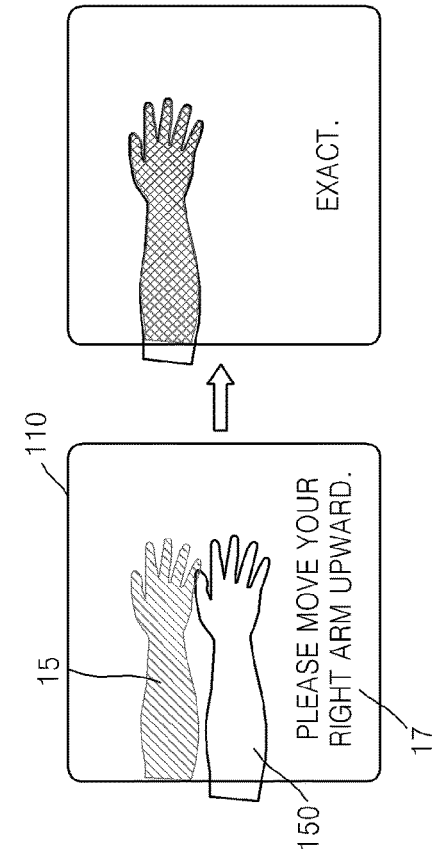
FIG. 12A
FIG. 12C
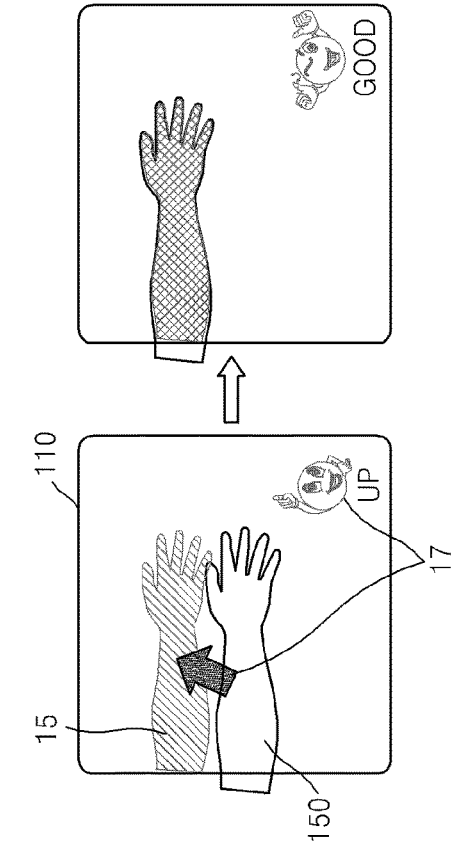
FIG. 12B
FIG. 12D

METHOD AND APPARATUS FOR PROVIDING INFORMATION RELATED TO LOCATION OF TARGET OBJECT ON MEDICAL APPARATUS

CROSS-REFERENCE TO RELATED PATENT APPLICATION

This application claims the benefit of Korean Patent Application No. 10-2013-0073966, filed on Jun. 26, 2013, in the Korean Intellectual Property Office, the disclosure of which is incorporated herein in its entirety by reference.

BACKGROUND

1. Field

The embodiments of this application relate to a method and apparatus for providing information regarding a location of a target object through a medical apparatus, and more particularly, to a method and apparatus for providing at least one of recommended location information of a target object and additional information for suitable photographing conditions.

2. Description of the Related Art

An X-ray is an electromagnetic wave having a wavelength of about 0.01*0.1 nm to about 100*0.1 nm, and may be generally used in a medical apparatus photographing the inside of a living body, or a non-invasive inspection apparatus in a field of the general industry due to a attribute of transmitting through an object.

An image capturing apparatus using an X-ray basically transmits an X-ray emitted from an X-ray tube (or X-ray source) through a target object, and determines an internal structure of the target object by detecting a difference between the intensities of the transmitted X-ray by using an X-ray detector. The internal structure of the target object may be easily determined based on a principle that the transmittance of the X-ray varies depending on a density of the target object and an atomic number of atoms of the target object. If a wavelength of the X-ray is short, a transmittance increases and an image becomes brighter.

An image capturing apparatus using an X-ray may generally include an X-ray source, an X-ray detector, and an image processor. The X-ray source irradiates an X-ray according to predetermined X-ray irradiation conditions, and the X-ray detector obtains image data based on the X-ray that has transmitted through the target object and transmits the image data to the image processor. The image processor processes the image data to display an image of the target object on a display unit.

That is, in the image capturing apparatus using the X-ray, when the X-ray emitted from the X-ray source transmits through the target object, a scintillator of the image capturing apparatus converts the X-ray into a visible ray according to a density of the target object, and the converted visible ray may be changed into an electric signal by a photodiode included in the image capturing apparatus using the X-ray. The image capturing apparatus using the X-ray may display a digital image of the target object through which the X-ray is transmitted by using the electric signal.

SUMMARY

The embodiments of this application provide a method and apparatus for providing information regarding a location of a target object via a medical apparatus.

According to an aspect, there is provided a method of providing information regarding a location of a target object through a medical apparatus, the method including: setting photographing conditions about the target object; acquiring current location information of the target object; acquiring recommended location information of the target object according to the photographing conditions; outputting the acquired recommended location information; comparing the current location information with the recommended location information; and outputting additional information about a current location of the target object, according to a comparison result.

The medical apparatus may include an X-ray apparatus, and the photographing conditions may include conditions about at least one of a location of an X-ray tube, a size of the collimation, a location of an X-ray detector, and a resolution of an image.

The photographing conditions may be set based on attribute information of the target object.

The acquiring of the current location information of the target object may include: acquiring an image including the target object by using at least one camera under the set photographing conditions; and extracting a contour line of the target object from the image.

The current location information may include information about the contour line.

The acquiring the recommended location information may include: acquiring a reference image related to the target object; and extracting a contour line of a region included in the reference image and corresponding to the target object.

The recommended location information may include information about the contour line.

The reference image may have a maximum clarity on a portion of the target object, which is to be photographed, under the set photographing conditions.

The outputting of the recommended location information may include projecting the recommended location information toward the target object.

The comparing of the current location information and the recommended location information may include determining a similarity between the current location information and the recommended location information.

The outputting of the additional information about the current location of the target object according to the comparison result may include outputting at least one of information regarding a correction of a location of the target object and information representing the similarity.

The additional information may be output in at least one of text, sound, and an image.

The outputting of the recommended location information may include: generating a composite image by overlapping the image with the contour line of the region; and displaying the generated composite image.

The composite image may be displayed on a display unit that is provided on at least a side of the X-ray source and the X-ray detector.

The display unit may include at least one of a liquid crystal display (LCD) panel, a projector, and a head-mounted display (HMD).

The projector may include an image transfer unit.

The comparing of the current location information with the recommended location information may include determining a similarity between the current location information and the recommended location information.

The outputting of the additional information about the current location of the target object according to the comparison result may include outputting at least one of information for correcting the location of the target object and information for representing the similarity.

The additional information may be output in at least one of text, sound, and an image.

The recommended location information may be variable depending on attribute information of the target object, and the recommended location information that is variable may be stored to correspond to the attribute information of the target object.

According to another aspect of the embodiments, there is provided an apparatus for providing information regarding a location of a target object through a medical apparatus, the apparatus including: a photographing condition setting unit for setting photographing conditions with respect to the target object; a current location information acquiring unit for obtaining current location information of the target object; a recommended location information acquiring unit for obtaining recommended location information of the target object according to the set photographing conditions; an information output unit for outputting the recommended location information; and a comparison unit for comparing the current location information with the recommended location information, wherein additional information about a current location of the target object may be output by the information output unit according to a comparison result of the comparison unit.

The medical apparatus may include an X-ray apparatus.

The photographing conditions may include conditions about at least one of a location of an X-ray tube, a size of the collimation, a location of an X-ray detector, and a resolution of an image.

The photographing conditions may be set based on attribute information of the target object.

The current location information acquiring unit may include: a first image obtaining unit for obtaining an image including the target object by using at least one camera under the set photographing conditions; and a first contour line extraction unit for extracting a contour line of the target object from the image, wherein the current location information may include information about the contour line.

The recommended location information acquiring unit may include: a second image acquiring unit for obtaining a reference image related to the target object; and a second contour line extraction unit for extracting a contour line of a region included in the reference image and corresponding to the target object.

The recommended location information may include information about the contour line of the region.

The reference image may have a maximum clarity on a portion of the target object, which is to be photographed, under the set photographing conditions.

The information output unit may include a projector for projecting the recommended location information toward the target object.

The comparison unit may include a similarity determining unit for determining a similarity between the current location information and the recommended location information.

The additional information may include at least one of information regarding a correction of a location of the target object and information representing the similarity.

The additional information may be output in at least one of text, sound, and an image.

The apparatus may further include a composite image generator for generating a composite image by overlapping the image with the contour line of the region, wherein the information output unit displays the generated composite image.

The information output unit may include a display unit that is provided on at least a side of the X-ray source and the X-ray detector.

The display unit may include at least one of a liquid crystal display (LCD) panel, a projector, and a head-mounted display (HMD).

The projector may include an image transfer unit.

The comparison unit may include a similarity determining unit for determining a similarity between the current location information and the recommended location information.

The additional information may be output in at least one of text, sound, and an image.

The recommended location information may be variable depending on attribute information of the target object, and the recommended location information that is variable may be stored to correspond to the attribute information of the target object.

According to another aspect of the embodiments, there is provided a computer-readable recording medium having embodied thereon a program for executing the above method.

According to another aspect of the embodiments there is provided a method including capturing a target image of a medical target associated with a medical apparatus, comparing the target image with a reference image, and providing information regarding location adjustment of the medical target relative to the medical apparatus responsive to the comparing.

The comparing may compares a reference contour of the reference image with a target contour of the target image.

The information regarding location adjustment can include one of a target movement direction and a composite image visually showing a difference between a current location and a reference location

BRIEF DESCRIPTION OF THE DRAWINGS

The above and other features and advantages embodiments will become more apparent by describing in detail exemplary embodiments thereof with reference to the attached drawings in which:

FIG. 2C is a diagram showing an example of providing recommended location information of a target object and additional information, according to another embodiment;

FIG. 5, including FIGS. 5A, 5B and 5C, is a diagram showing an example of acquiring current location information of the target object with a 2D camera, a stereo camera and a depth camera, according to the embodiment;

FIG. 7 is a diagram showing an example of acquiring recommended location information from a standard image, according to an embodiment;

FIGS. 11A through 11C are diagrams showing examples of determining similarity, according to an embodiment;

FIGS. 12A through 12D are diagrams showing examples of providing additional information, according to an embodiment;

DETAILED DESCRIPTION

Figure 1A:
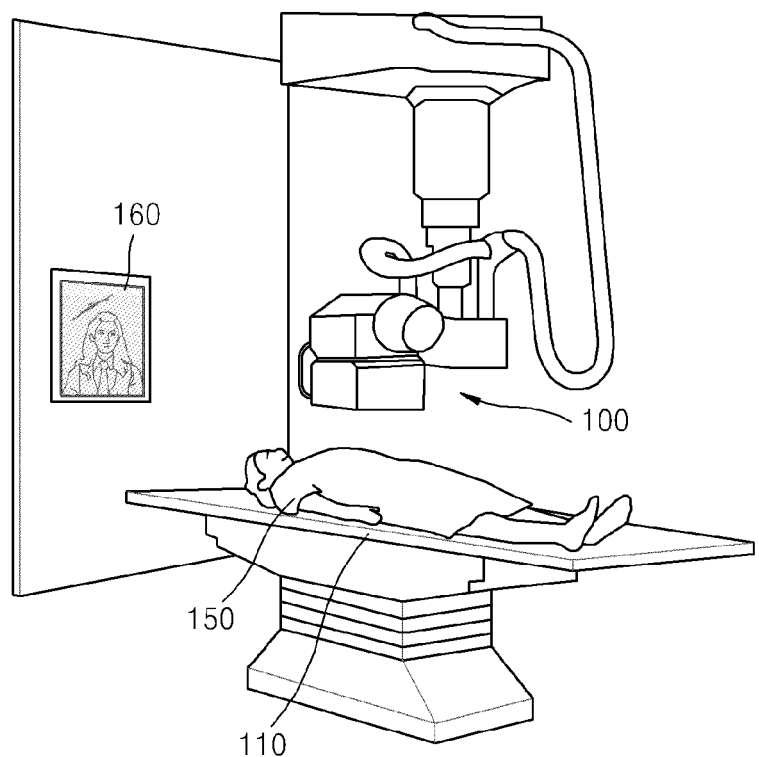
FIG. 1A is a diagram showing an example of diagnosis by using a general medical apparatus.

The attached drawings for illustrating exemplary embodiments are referred to in order to gain a sufficient understanding of the embodiments, the merits thereof, and the objectives accomplished by the implementation of the embodiments. The embodiments may, however, be embodied in many different forms and should not be construed as being limited to the embodiments set forth herein; rather, these embodiments are provided such that this disclosure will be thorough and complete, and will fully convey the concept to one of ordinary skill in the art.

Hereinafter, the terms used in the specification will be briefly described, and then the embodiments will be described in detail.

The terms used in this specification are those general terms currently widely used in the art in consideration of functions in regard to the embodiments, but the terms may vary according to the intention of those of ordinary skill in the art, precedents, or new technology in the art. Also, specified terms may be selected by the applicant, and in this case, the detailed meaning thereof will be described in the detailed description of the embodiments. Thus, the terms used in the specification should be understood not as simple names but based on the meaning of the terms and the overall description of the embodiments.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware such as FPGA or ASIC, software, or a combination of hardware and software. However, the "unit" is not limited to software or hardware. The "unit" may be configured to exist in a storage medium that is addressable, or may be configured to reproduce one or more processors. Therefore, as an example, the "unit" may include components such as software components, object-oriented software components, class components, and task components, processes, functions, attributes, procedures, sub-routines, segments of program code, drivers, firmware, micro codes, data, databases, data structures, tables, arrays, and variables. The components and functions provided in the "units" may be combined into a less number of components and "units", or may be divided into additional components and "units".

In the present specification, an "image" may denote multi-dimensional data configured by discrete image elements (for example, pixels in a two-dimensional image and voxels in a three-dimensional image). For example, an image may include medical images of an object acquired by an X-ray, a CT, an MRI, an ultrasound wave, and other medical image systems.

Also, in the present specification, a target object may include a human being or an animal, or a part of the human being or the animal. For example, the target object may include organs, such as the liver, the heart, the uterus, the brain, breasts, the abdomen, or blood vessels.

Also, the "target object" may include a phantom. The phantom denotes a material having a volume, a density, and an effective atomic number that is nearly equivalent to those of a living organism, and a phantom according to embodiments may be a spherical phantom having similar properties to those of the human body.

In the present specification, a "user" is a medical expert, for example, a doctor, a nurse, a medical specialist, and a medical imaging expert, or an engineer managing medical apparatuses; however, the embodiments are not limited thereto.

Embodiments will be described below in more detail with reference to the accompanying drawings. The components that are the same or are in correspondence are rendered the same reference numeral regardless of the figure number, and redundant explanations are omitted. Expressions such as "at least one of," when preceding a list of elements, modify the entire list of elements and do not modify the individual elements of the list.

An X-ray system is a medical image system that acquires images of internal structures of the human body by transmitting an X-ray through the human body. The X-ray system may acquire medical images of a target object more simply within a shorter time than other medical image systems including an MRI system and a CT system. Therefore, the X-ray system is widely used in a simple chest photographing, abdomen photographing, skeleton photographing, nasal sinuses photographing, neck soft tissue photographing, and breast photographing.

Figure 1B:
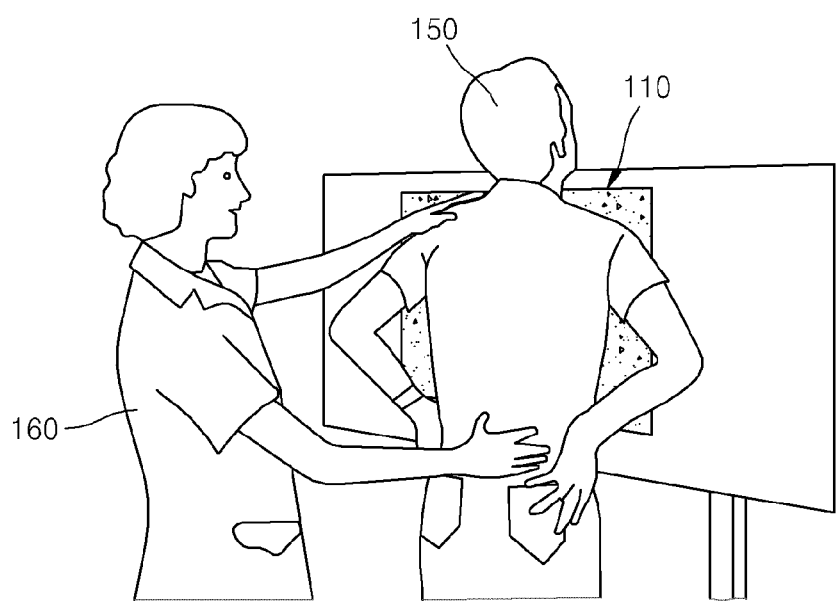
FIG. 1B is a diagram showing an example of correcting a location of a target object during diagnosis using the general medical apparatus.

FIG. 1A is a diagram showing an example of diagnosis by using a general medical apparatus. FIG. 1B shows an example of correcting a location of a target object during diagnosis using the general medical apparatus.

According to the general medical apparatus, a user of the general medical apparatus guides postures of a target object (for example, a patient) by using a sound (e.g., the user's voice) or directly touching the target object in an examination room.

As shown in FIG. 1A, the user of the general medical apparatus may guide the posture of the target object to be photographed, aurally by using a microphone in a shielded space outside the examination room.

For example, if the general medical apparatus is an X-ray apparatus, in order to diagnose a disease of a target object 150 located between an X-ray source 100 and an X-ray detector 110, a clear image, including a region to be diagnosed of the target object 150, has to be obtained. In order to obtain the clear image, movement of the target object 150 has to be suppressed as much as possible during a photographing operation, and the target object 150 has to maintain a right or correct posture.

As described above, in order to obtain a clear image of the target object 150, the target object 150 has to pose appropriately to be within an irradiation range of the X-ray emitted from the X-ray source 100 or an X-ray detection range of the X-ray detector 110. In addition, in order to guide the target object 150 to pose appropriately, a user 160 may use a microphone in a space shielded from the X-ray outside the examination room.

However, if the target object 150 is a kid, a foreigner, or is not capable of understanding instructions, it is difficult or impossible to guide the target object 150 to pose accurately only by the voice guidance of the user 160.

Also, if the photographing has to be performed while changing the posture of the target object 150, it is difficult to guide the posture of the target object 150 accurately only by the voice guidance of the user 160.

In addition, according to the general medical apparatus, the user 160 of the general medical apparatus may directly correct the posture of the target object 150 by touching the target object in the examination room.

However, the posture of the target object 150 may be changed while the user 160 exits the examination room after guiding the posture of the target object 150, and thus, the user 160 has to go back to the examination room to guide the posture of the target object 150 again. For example, if the target object 150 is a child, the target object 150 is likely to move frequently even when the user directly corrects (or guides) the posture of the target object 150, and thus, second, third corrections, etc. may be repeatedly performed.

Also, the direct and repeated corrections by the user 160 may increase the photographing time.

In addition, as described above, when the photographing has to be performed while changing the posture of the target object 150, it is difficult to guide the posture of the target object 150 accurately only by the voice of the user 160. Thus, the user 160 needs to go into the examination room to directly guide the posture of the target object 150, and accordingly, it takes a long time to correct the posture of the target object 150, and the time for preparing the photographing also increases.

Also, if the target object 150 refuses to be touched by the user 160, there is no way to guide the posture of the target object 150, except by the voice guidance.

Also, in the point of view of the target object 150, the target object 150 (e.g., patient) may not get feedback about the posture or how the posture has to be corrected when the target object 150 is asked by the user 160 to correct the posture.

In addition, according to the related art, the target object 150 (e.g., patient) may not get any feedback about a preparing status of photographing and photographing procedures, and thus, the patient may be curious about whether the diagnosis is performed or not, or may feel uncomfortable.

Also, according to the related art, a preliminary photographing operation is performed, and then, a re-photographing operation may be performed. However, in this case, an amount of radiation to the patient is increased.

Also, at the user 160's end, the user 160 may not receive information about a recommended location for each photographing area of the target object 150, and thus, if the user 160 is not a skilful operator, the target object 150 has to be photographed a plurality of times in order to obtain effective images. The repeated photographing operations may increase the radiation amount of the target object 150, and also, photographing costs and the photographing time increase. Thus, the efficiency of a photographing operation may be degraded.

Also, even if the user 160 is accustomed to the photographing operation, the posture of the target object 150 has to be guided independently according to the features of the target object 150 (for example, physical attribute of the patient), and thus, the time taken for guiding the posture of the target object 150 may be increased.

In addition, it is difficult for the user 160 to determine a matching rate between the current location (or posture) of the target object 150 and a recommended posture, and thus, the user 160 generally has to perform the photographing operation depending on the experience of the user 160.

That is, according to the general method of guiding the posture of the target object 150, a time for preparing the photographing operation of the target object 150 may increase or the photographing operation has to be performed a plurality of times according to the skill of the user 160 or a status of the target object 150. Further, the photographing operation may harmfully affect the health of the target object 150, and photographing costs and the photographing time also increase.

Figure 1C:
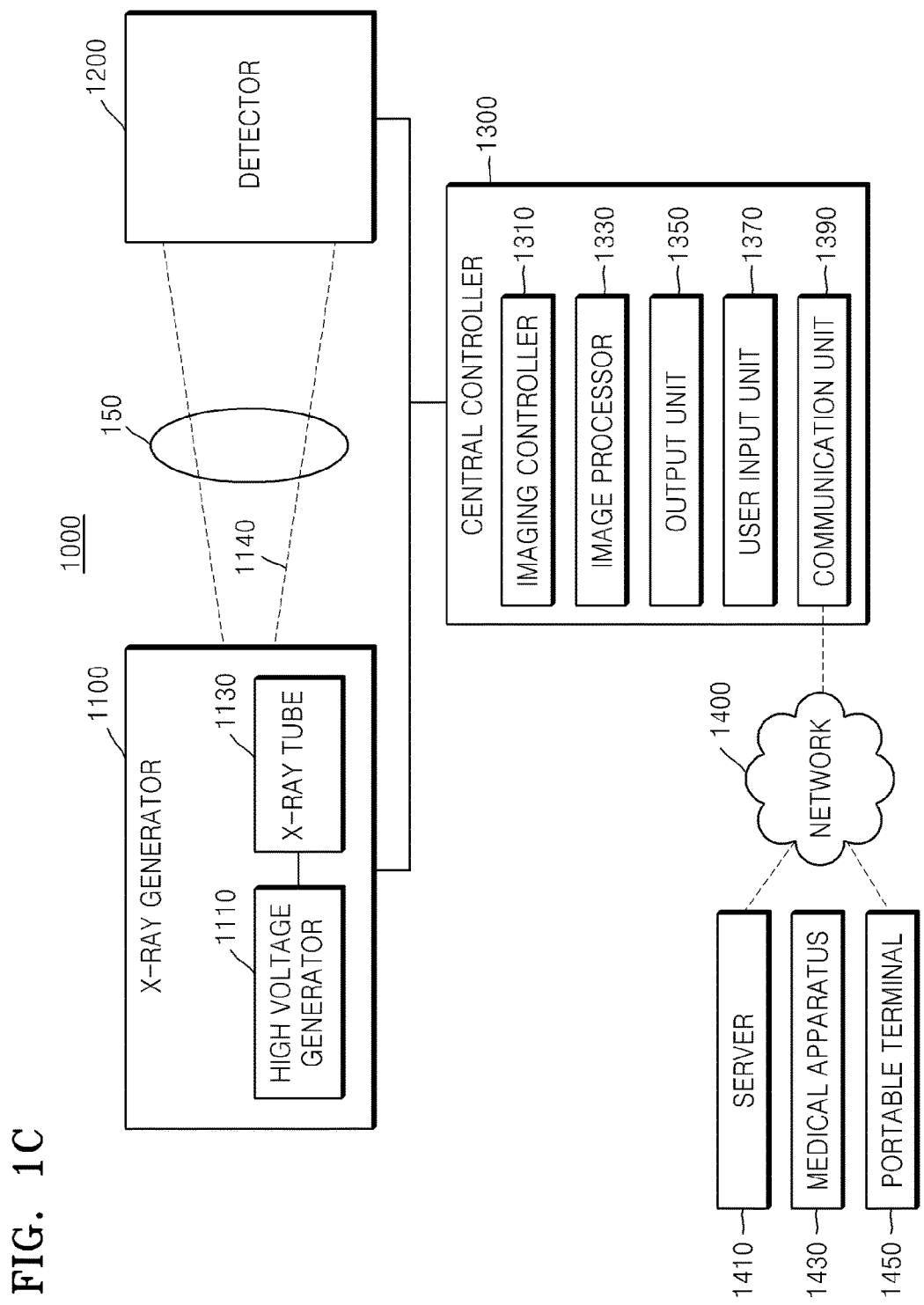
FIG. 1C is a schematic diagram of an X-ray apparatus according to an embodiment.
Figure 10:
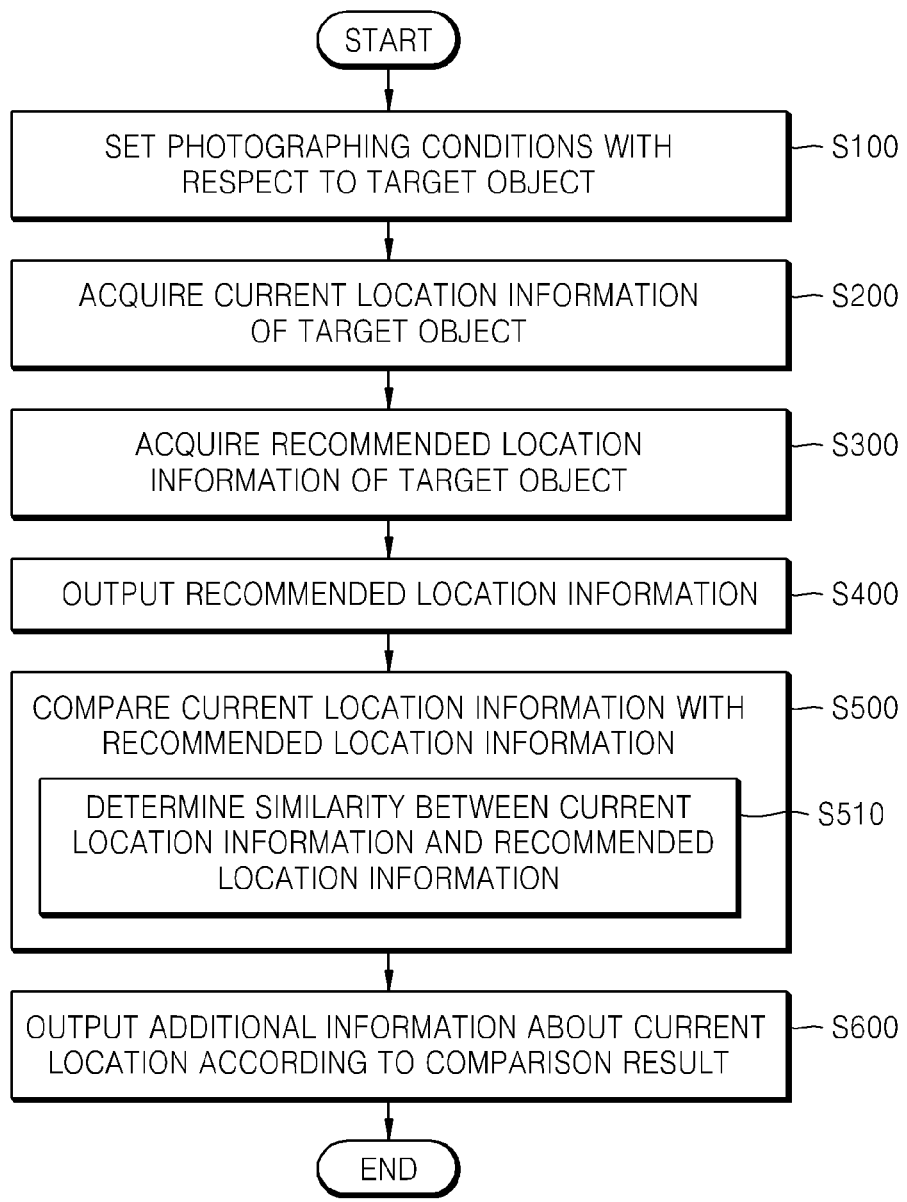
FIG. 10 is a flowchart illustrating a method of comparing current location information with recommended location information, according to an embodiment.

FIG. 1C is a schematic diagram of an X-ray apparatus 1000 according to an embodiment. Referring to FIG. 10, the X-ray apparatus 1000 may include an X-ray generator 1100, an X-ray detector 1200, and a central controller 1300. The X-ray apparatus 1000 shown in FIG. 10 may be a fixed-type X-ray apparatus or a mobile X-ray apparatus.

The X-ray generator 1100, the X-ray detector 1200, and the central controller 1300 may be connected to each other via wires or wirelessly. If they are connected to each other wirelessly, a device (not shown) for synchronizing clocks with each other may be further included.

The X-ray generator 1100 irradiates an X-ray 1140 to a target object 150. The target object 150 may be located between the X-ray generator 1100 and the X-ray detector 1200, and may stand or lie on a table. The X-ray generator 1100 may be referred to as an X-ray source.

The X-ray generator 1100 may include a high voltage generator 1110 and an X-ray tube 1130. The X-ray tube 1130 may include an X-ray source (not shown) and a collimator (not shown).

The high voltage generator 1110 generates a high voltage current according to a command of the central controller 1300, and transfers the electric current to the X-ray source of the X-ray tube 1130. The X-ray source generates the X-ray 1140 by using the high voltage current generated by the high voltage generator 1110. A wavelength of the X-ray 1140 is adjusted according to a magnitude of the voltage, and an intensity of the X-ray 1140 is adjusted according to the current intensity.

The collimator controls a direction and a width of the X-ray 1140 that is irradiated to the target object 150. According to the operation of the collimator, the X-ray 1140 may accurately reach a region of interest of the target object 150, and an amount of radiation of the X-ray 1140 to the target object 150 may be reduced.

The X-ray detector 1200 receives the X-ray 1140 transmitted through the target object 150 or around the target object 150, and generates image data corresponding to an intensity of the received X-ray 1140. The X-ray generator 1100 and the X-ray detector 1200 may be variously located with the target object 150 therebetween. The X-ray detector 1200 may include a wired detector or a wireless detector.

The central controller 1300 transmits operation timing information and photographing conditions to the X-ray generator 1100 and the X-ray detector 1200, and generates a medical image of the target object 150 based on the image data transmitted from the X-ray detector 1200. If the X-ray apparatus 1000 is a fixed-type X-ray apparatus, the central controller 1300 may be located in an examination room unlike the X-ray generator 1100 and the X-ray detector 1200, and may receive input of the photographing conditions and predetermined control information for taking medical images from a user.

The central controller 1300 may include an imaging controller 1310, an image processor 1330, an output unit 1350, a user input unit 1370, and a communication unit 1390.

The imaging controller 1310 controls locations of the X-ray generator 1100 and the X-ray detector 1200 according to predetermined photographing conditions, photographing timings, and the photographing conditions.

In particular, the imaging controller 1310 controls the high voltage generator 1110 and the X-ray tube 1130 according to a photographing start input received through the user input unit 1370 in order to control a timing of irradiating the X-ray 1140, a wavelength of the X-ray 1140, the intensity of the X-ray 1140, and an irradiation range of the X-ray 1140. Also, the imaging controller 1310 adjusts the location of the X-ray detector 1200 according to the predetermined photographing conditions, and controls a timing of operating the X-ray detector 1200.

The image processor 1330 generates the medical image of the target object 150 based on the image data transmitted from the X-ray detector 1200. In particular, the image processor 1330 receives the image data from the X-ray detector 1200, and then, generates the medical image of the target object 150 by removing noise of the image data and controlling a dynamic range and interleaving of the image data.

The output unit 1350 may output the medical image generated by the image processor 1330. Also, the output unit 1350 may output information that is necessary for the user to manipulate the X-ray apparatus 1000, for example, a user interface (UI), user information, or target object information. The output unit 1350 may include a speaker, a printer, a cathode ray tube (CRT) display, a liquid crystal display (LCD), a plasma display panel (PDP) display, an organic light-emitting diode (OLED) display, a field emission display (FED), a light-emitting diode (LED) display, a vacuum fluorescent display (VFD), a digital light processing (DLP) display, a primary flight display (PFD), a three-dimensional (3D) display, a transparent display, et al.

The user input unit 1370 receives a predetermined input from the user. The user input unit 1370 may include a keyboard, a mouse, a touch screen, a voice recognizer, a fingerprint recognizer, an iris recognizer, and the like. The user may input the photographing conditions and predetermined control information by using the user input unit 1370.

Also, the user input unit 1370 may include a switch for receiving a photographing start command from the user. According to embodiments, the switch may be configured so that the user has to press the switch twice in order to input an X-ray irradiation command. That is, when the user presses the switch, a prepare command for indicating a pre-heat for irradiating the X-ray, and when the user presses the switch once more, an irradiation command for actually irradiating the X-ray may be input. As such, when the user manipulates the switch, the switch generates signals corresponding to the input commands, that is, a prepare signal and an irradiation signal, and outputs the signals to the high voltage generator 1110.

The communication unit 1390 may be connected to a network 1400 via wires or wirelessly to communicate with an external server 1410, an external medical apparatus 1430, or an external portable terminal 1450.

The communication unit 1390 may transmit/receive data relating to the diagnosis of the target object 150 via the network 1400, and may receive medical images taken by another medical apparatus 1430, such as a CT, an MRI, or another X-ray apparatus. Moreover, the communication unit 1390 may receive a diagnosis history or a treatment schedule of the target object 150 from the external server 1410 to diagnose a disease of the target object 150. Also, the communication unit 1390 may perform data communication with the external portable terminal 1450, such as a mobile phone, a personal digital assistant (PDA), or a laptop computer of a doctor or a patient, as well as the external server 1410 or the external medical apparatus 1430 in a hospital.

The communication unit 1390 may include one or more elements enabling to communicate with external devices, for example, a short distance communication module, a wired communication module, and a wireless communication module.

The short distance communication module is a module for communicating with a device located within a predetermined distance. The short distance communication technology may be wireless local area network (LAN), Wi-Fi, Bluetooth, Zigbee, Wi-Fi Direct (WFD), ultra wideband (UWD), infrared data association (IrDA), Bluetooth low energy (BLE), near field communication (NFC), or the like; however, the embodiments are not limited thereto.

The wired communication module is a module for communicating by using an electric signal or an optical signal, and the wired communication technology may be wired communication technology using a pair cable, a coaxial cable, or an optical fiber cable, and a wired communication technology that is well known in the art.

The wireless communication module may transmit/receive a wireless signal to/from at least one of the base, an external device, and a server in a mobile communication network. Here, the wireless signal may be a voice call signal, a video call signal, or various types of data according to text/multimedia messages transmission.

The X-ray apparatus 1000 shown in FIG. 10 may include a plurality of digital signal processors (DSPs), an ultra-small calculator, and a processing circuit for specialized usage (for example, a high speed analog/digital (A/D) conversion, a high speed Fourier transformation, an array process, etc.).

The communication between the X-ray generator 1100 and the central controller 1300, and between the X-ray detector 1200 and the central controller 1300 may use a high speed digital interface, such as low voltage differential signalling (LVDS), asynchronous serial communication, such as universal asynchronous receiver transmitter (UART), synchronous serial communication, or a low latency network protocol, such as a controller area network (CAN), and other various communication methods that are well known in the art may be used.

Also, the communication between the central controller 1300 and the user input unit 1370 may be performed by using gigabit Ethernet (registered trademark), or other various communication methods that are well known in the art.

Figure 1D:
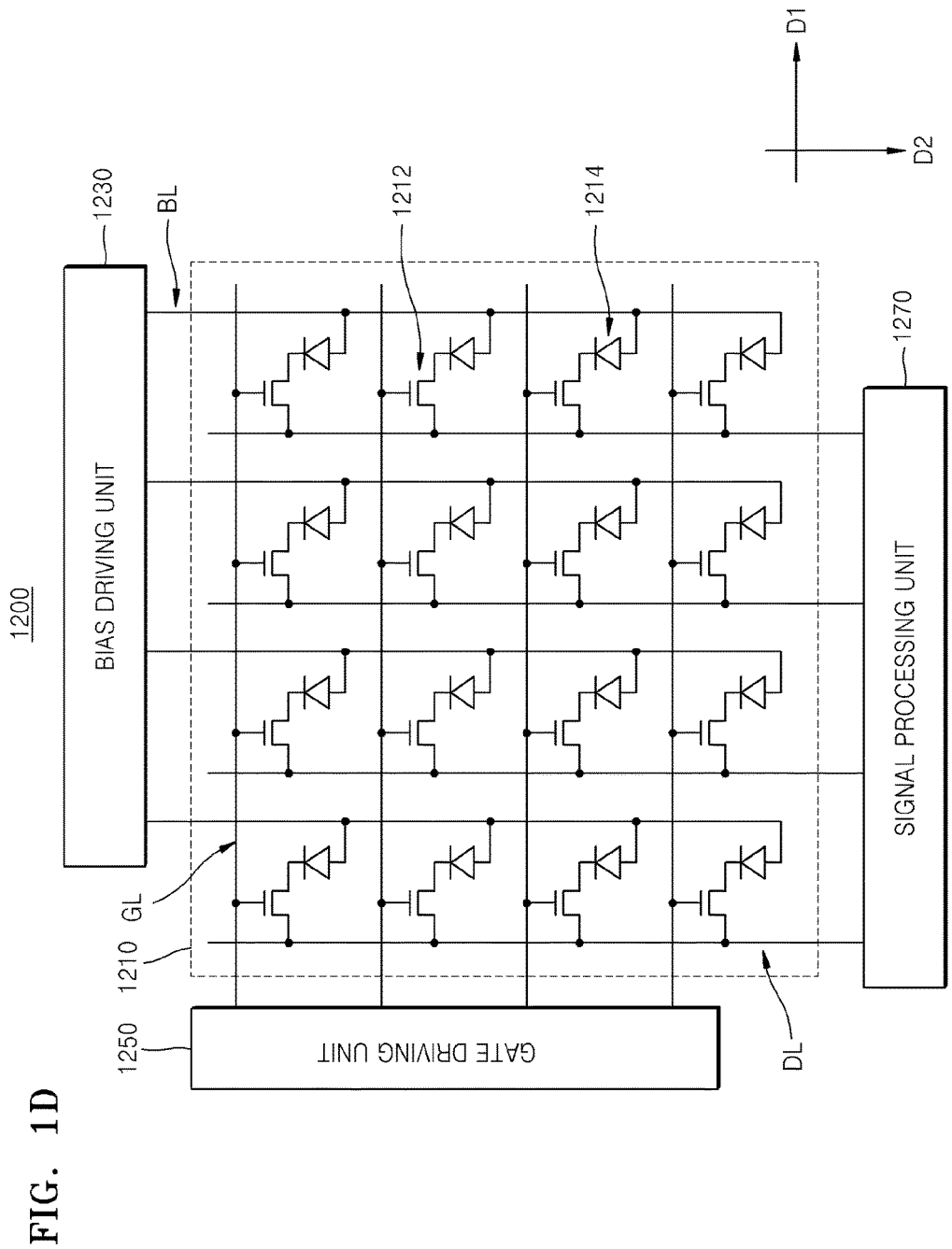
FIG. 1D is a diagram showing a detailed configuration of an X-ray detector shown in FIG. 1C, according to an embodiment.

FIG. 1D shows a detailed configuration of the X-ray detector 1200 shown in FIG. 1C, according to an embodiment.

Referring to FIG. 1D, the X-ray detector 1200 may include a photodetecting substrate 1210, a bias driving unit 1230, a gate driving unit 1250, and a signal processing unit 1270.

The photodetecting substrate 1210 receives the X-ray from outside to form a photodetecting voltage. The photodetecting substrate 1210 may include gate lines GL, data lines DL, thin film transistors (TFTs) 1212, photodiodes 1214, and bias lines BL.

The gate lines GL may be formed in a first direction D1, and the data lines DL may be formed in a second direction D2 that crosses the first direction D1. The first direction D1 and the second direction D2 may be perpendicular to each other. In FIG. 1D, four gate lines GL and four data lines DL are shown as an example.

The TFTs 1212 may be arranged as a matrix in the first and second directions D1 and D2. Each of the TFTs 1212 may be electrically connected to one of the gate lines GL and one of the data lines DL. A gate of the TFT 1212 is electrically connected to the gate line GL, and a source of the TFT 1212 may be electrically connected to the data line DL. In FIG. 1D, sixteen TFTs 1212 (4×4) are shown as an example.

The photodiodes 1214 may be arranged as a matrix in the first and second directions D1 and D2 so as to correspond to the TFTs 1212 in one-to-one correspondence. Each of the photodiodes 1214 may be electrically connected to one of the TFTs 1212. An N-side terminal of each of the photodiodes 1214 may be electrically connected to a drain of each TFT 1212. FIG. 1D shows sixteen photodiodes 1214 (4×4) as an example.

Each of the photodiodes 1214 receives the X-ray from outside to form a photodetecting voltage. The photodetecting voltage may correspond to an intensity of the X-ray. The photodetecting voltage may be generated at the N-side terminal of the photodiode 1214.

The bias lines BL are electrically connected to the photodiodes 1214. Each of the bias lines BL may be electrically connected to a P-side terminal of each of the photodiodes 1214 arranged in a direction. For example, the bias lines BL may be formed to be substantially parallel with the second direction D2 to be electrically connected to the photodiodes 1214. Otherwise, the bias lines BL may be formed to be substantially parallel with the first direction D1 to be electrically connected to the photodiodes 1214. FIG. 1D shows four bias lines BL formed along the second direction D2 as an example.

The bias driving unit 1230 is electrically connected to the bias lines BL so as to apply a driving voltage to the bias lines BL. The bias driving unit 1230 may selectively apply a reverse bias or a forward bias to the photodiodes 1214. A reference voltage may be applied to the N-side terminal of the photodiode 1214. The bias driving unit 1230 may apply a voltage that is less than the reference voltage to the P-side terminal of the photodiode 1214 so as to apply a reverse bias to the photodiode 1214. Otherwise, the bias driving unit 1230 may apply a voltage that is greater than the reference voltage to the P-side terminal of the photodiode 1214 so as to apply a forward bias to the photodiode 1214.

The gate driving unit 1250 is electrically connected to the gate lines GL to apply gate signals to the gate lines GL. The gate driving unit 1250 sequentially applies the gate signals to the gate lines GL along the second direction D2. For example, when the gate signals are applied to the gate lines GL, the gate signals may turn the TFTs 1212 on. On the other hand, when the gate signals are not applied to the gate lines GL, the gate signals may turn the TFTs 1212 off.

The signal processing unit 1270 is electrically connected to the data lines DL to receive sample input voltages from the data lines DL. The signal processing unit 1270 may output image data to the outside by using the sample input voltages. The image data may be an analog signal or a digital signal corresponding to the photodetecting voltage.

Although not shown in FIG. 1D, if the X-ray detector 1200 shown in FIG. 1D is a wireless detector, the X-ray detector 1200 may further include a battery unit and a wireless communication interface.

Figure 1E:
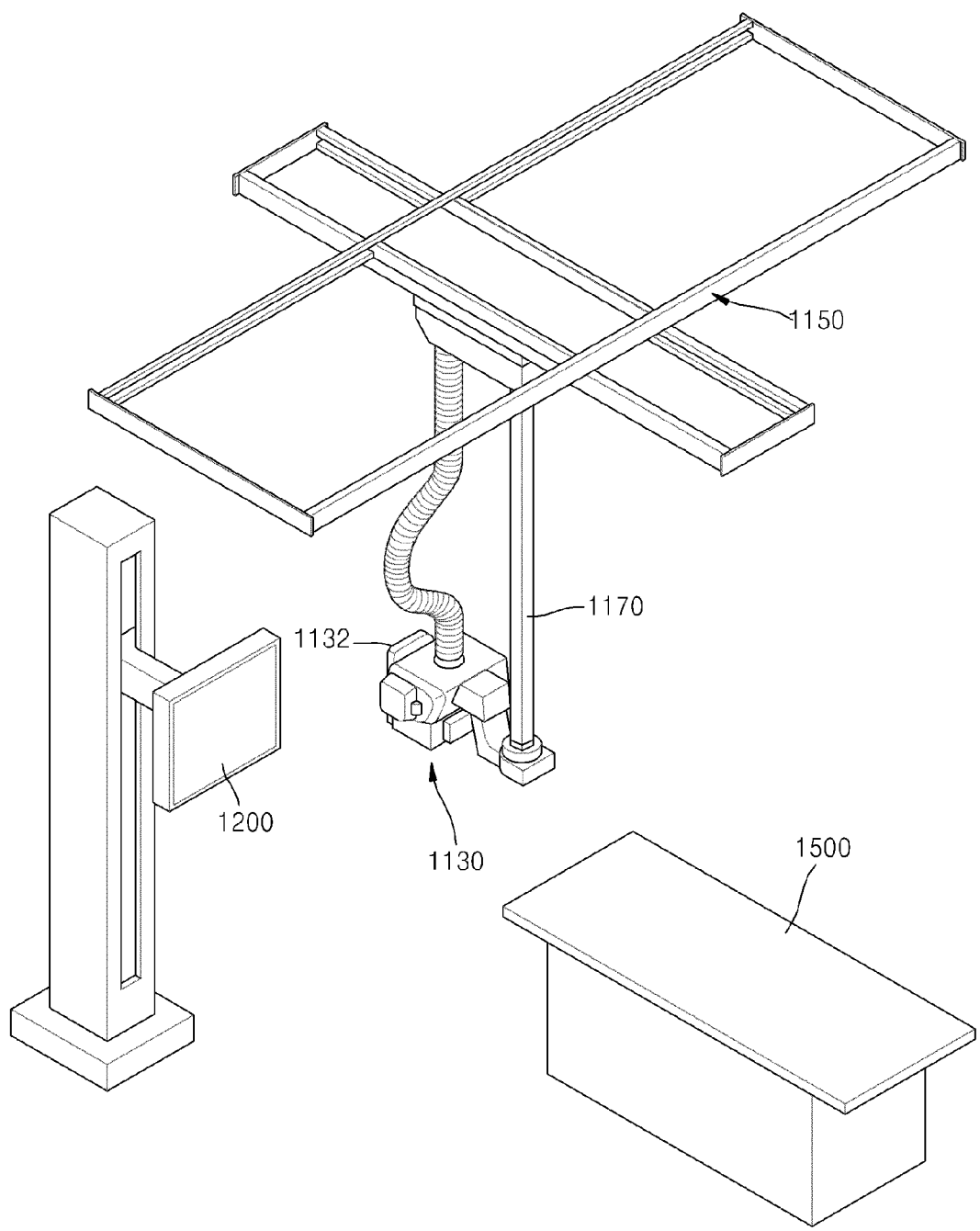
FIG. 1E is a perspective view showing a fixed-type X-ray apparatus according to an embodiment.

FIG. 1E is a perspective view showing an example of a fixed-type X-ray apparatus according to an embodiment.

As shown in FIG. 1E, the fixed-type X-ray apparatus includes an X-ray tube 1130 for irradiating the X-ray to the target object 150, an X-ray detector 1200 for detecting the X-ray transmitted through the target object 150, and a guide rail 1150 and a post 1170 for guiding movement of the X-ray tube 1130.

The X-ray tube 1130 generates the X-ray by using a high voltage current transferred from the high voltage generator 1110, and irradiates the X-ray to the target object 150. A manipulation unit 1132 providing a UI through which information about the photographing is input and each element may be manipulated may be connected to a side surface of the X-ray tube 1130.

The X-ray detector 1200 detects the X-ray transmitted through the target object 150. As shown in FIG. 1E, the X-ray detector 1200 may be configured to move in an up-and-down direction, and may be located under a table 1500 that supports the target object 150.

The guide rail 1150 may be provided on a ceiling of an examination room in which the fixed-type X-ray apparatus is disposed. A moveable roller (not shown) may be mounted on the guide rail 1150, and the X-ray tube 1130 may move along the guide rail 1150.

The post 1170 may be located between the X-ray tube 1130 and the guide rail 1150. A length of the post 1170 may increase or decrease, and accordingly, a height of the X-ray tube 1130 may be adjustable.

FIG. 1E shows the fixed-type X-ray apparatus that is connected to the ceiling of the examination room; however, the fixed-type X-ray apparatus shown in FIG. 1E is just an example for convenience of description, and the fixed-type X-ray apparatus according to embodiments may be an X-ray apparatus having various structures, for example, a C-arm-type X-ray apparatus and a robot arm-type X-ray apparatus.

Figure 1F:
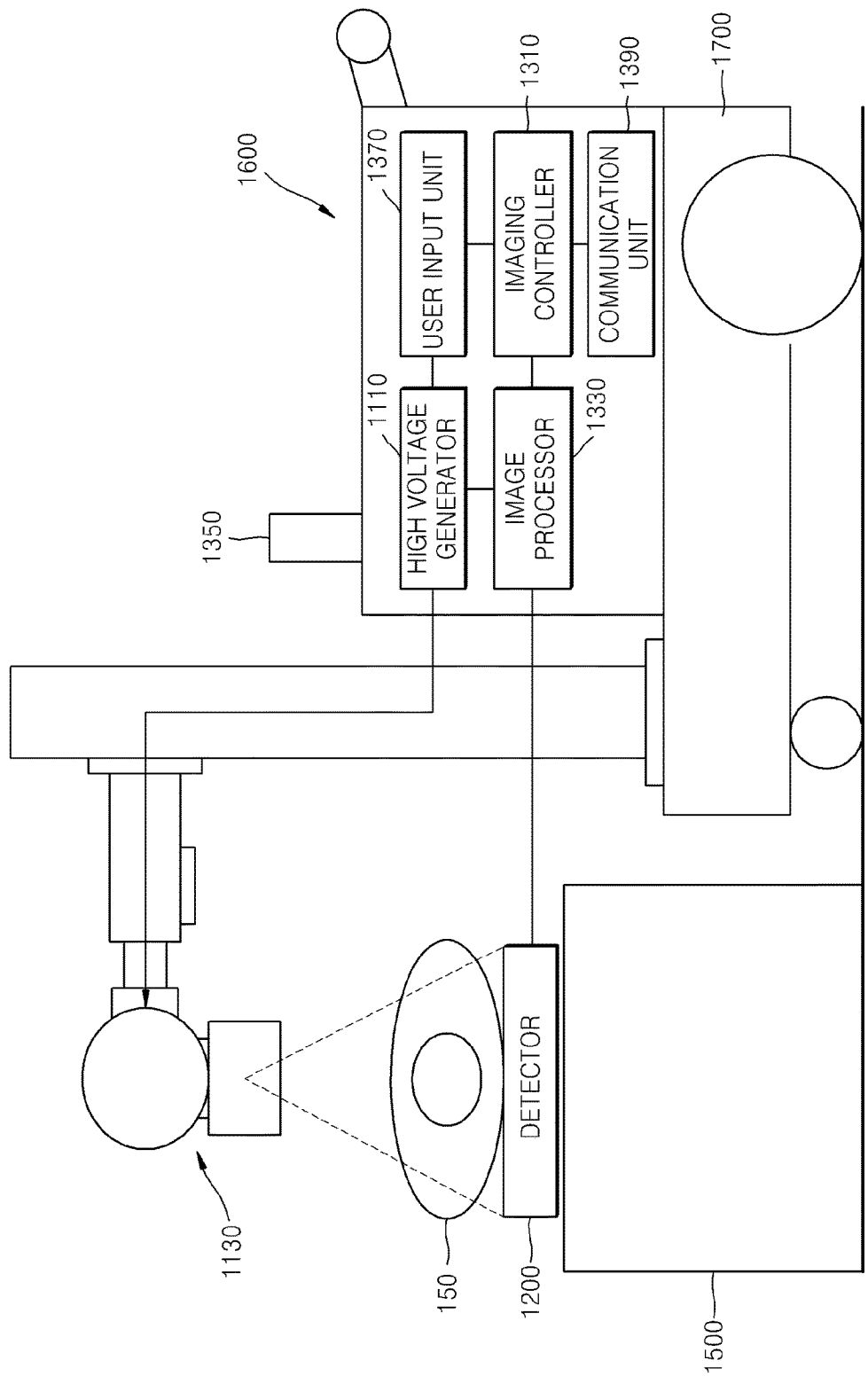
FIG. 1F is a diagram of a mobile X-ray apparatus according to an embodiment.

FIG. 1F is a diagram showing a configuration of a mobile X-ray apparatus according to an embodiment.

Referring to FIG. 1F, the mobile X-ray apparatus includes the elements shown in FIG. 1C, and in particular, components of the central controller 1300 and the high voltage generator 1110 shown in FIG. 1C are built in a main body 1600 of the mobile X-ray apparatus.

Also, the mobile X-ray apparatus may further include a moving unit 1700 enabling the mobile X-ray apparatus to move.

The high voltage generator 1110 generates a high voltage current according to a control command of the imaging controller 1310, and transmits the generated electric current to the X-ray tube 1130. The X-ray source included in the X-ray tube 1130 generates the X-ray, and the generated X-ray transmits through the collimator to be irradiated onto the target object 150.

The X-ray detector 1200 detects the X-ray transmitted through the target object 150 and transmits image data to the image processor 1330.

The imaging controller 1310 controls locations of the high voltage generator 1110, the X-ray tube 1130, and the X-ray detector 1200 according to predetermined photographing conditions, a photographing timing, and the photographing conditions.

The image processor 1330 generates a medical image of the target object 150 based on the image data transmitted from the X-ray detector 1200. In particular, the image processor 1330 receives the image data from the X-ray detector 1200, and then, generates the medical image of the target object 150 by removing noise of the image data and adjusting a dynamic range and an interleaving of the image data.

The output unit 1350 may output the medical image generated by the image processor 1330. Also, the output unit 1350 may output information that is necessary for a user to manipulate the mobile X-ray apparatus, such as a UI, user information, or target object information.

The user input unit 1370 receives a predetermined input from the user. The user input unit 1370 may include a keyboard, a mouse, a touch screen, a voice recognizer, a fingerprint recognizer, or an iris recognizer, and other input devices that are well known in the art. The user may input the photographing conditions of the medical image and predetermined control information by using the user input unit 1370.

The communication unit 1390 is connected to a network through a wire or wirelessly to communicate with an external server, an external medical apparatus, or an external portable terminal.

Figure 2A:
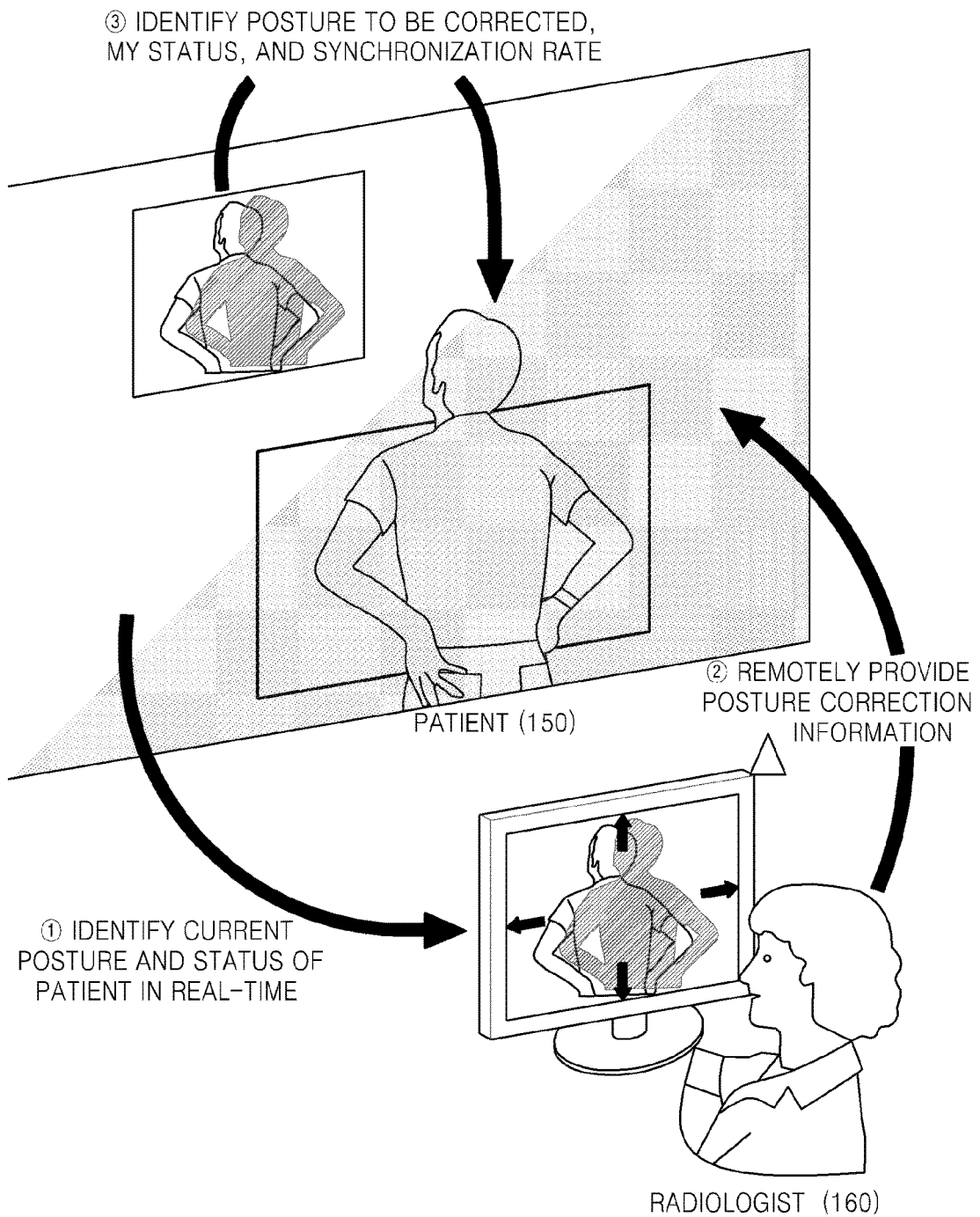
FIG. 2A is a schematic diagram illustrating a method of providing recommended location information of a target object and additional information, according to an embodiment.

FIG. 2A is a schematic diagram illustrating a method of providing recommended location information of a target object and additional information, according to an embodiment.

According to the present embodiment, the user 160 may identify a status of the target object 150, such as a current location or a posture, a type of target part location, of the target object 150, in real-time. As described above, the target object 150 according to the present embodiment may be a patient.

The user 160 may provide the target object 150 with posture correction information from a place shielded from an examination room where the target object 150 is. The posture correction information may be projected directly onto the target object 150 or may be provided through a predetermined device having a display. Also, the posture correction information may be provided via a wired communication or a wireless communication.

The target object 150 may check the current status, the posture to be corrected, and a synchronization (or matching) rate with a recommended location in real-time by using the posture correction information provided from the user 160. Also, the target object 150 may correct his/her own posture according to the posture correction information.

Figure 2B:
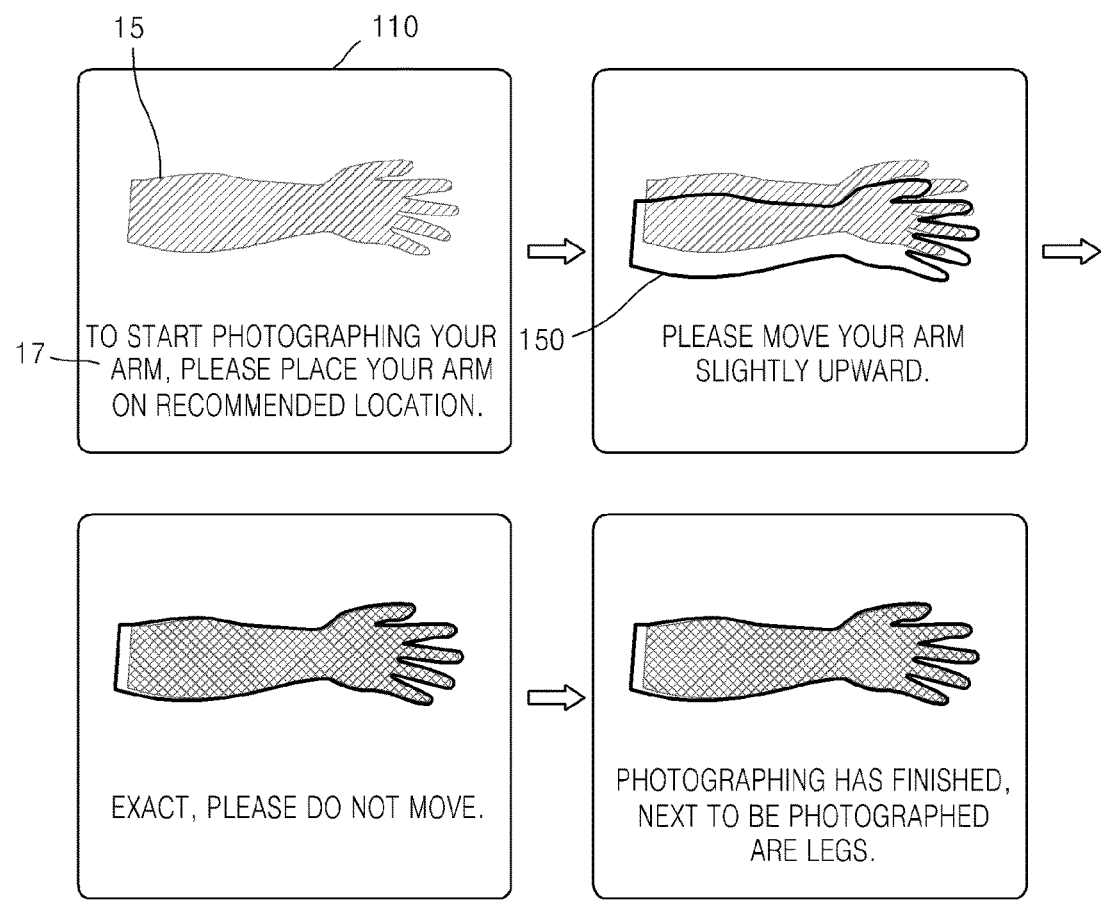
FIG. 2B is a diagram showing an example of providing recommended location information of a target object and additional information, according to an embodiment.

FIG. 2B shows an example of providing recommended location information of the target object 150 and additional information, according to an embodiment.

According to the present embodiment, recommended location information 15 may be provided to an X-ray detector 110. Also, additional information 17 related to the photographing operation may be provided to the X-ray detector 110. As shown in FIG. 2B, one of the recommended location information 15 and the additional information 17 may be provided on the X-ray detector 110.

For example, an arm of the target object 150 is to be photographed, and guidance information about the photographing processes may be provided to the target object 150 as additional information 17. The target object 150 may recognize the photographing process status by using at least one of the recommended location information 15 and the additional information 17, and thus, may actively participate in the photographing process.

According to the present embodiment, at least one of the recommended location information 15 and the additional information 17 may be projected onto the X-ray detector 110, for example, via a projector. That is, according to the present embodiment, as shown in FIG. 2B, at least one of the recommended location information 15 and the additional information 17 may be directly provided on the target object 150.

FIG. 2C shows an example of providing recommended location information of a target object and additional information, according to another embodiment.

According to the present embodiment, at least one of recommended location information 15 and additional information 17 may be included in a composite image 30 to be provided.

As shown in FIG. 2C, at least one of the recommended location information 15 and the additional information 17 may be combined with a current image of the target object 150, and may be provided as the composite image 30.

In addition, as shown in FIG. 2C, when the chest of the target object 150 is photographed, for example, at least one of the recommended location information 15 and the additional information 17 may be provided to the target object 150 as the composite image 30 according to the photographing process. The target object 150 may recognize the proceeding state of the photographing by using the at least one of the recommended location information 15 and the additional information 17, and may actively participate in the photographing operation.

The composite image 30, including at least one of the recommended location information 15 and the additional information 17, according to the embodiment may be provided via a device having a display function, such as an LCD panel.

Figure 3:
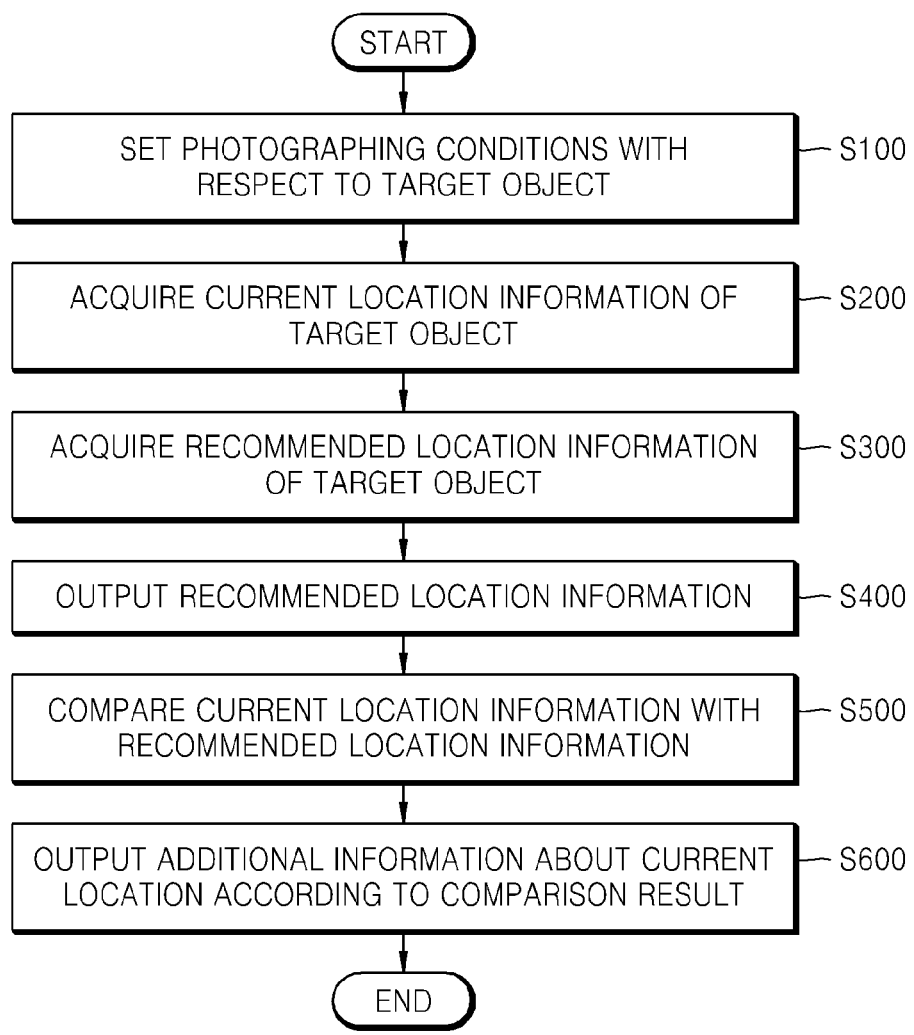
FIG. 3 is a flowchart illustrating a method of providing information regarding a location of a target object through a medical apparatus, according to an embodiment.

FIG. 3 is a flowchart illustrating a method of providing information related to a location of an object 150 via a medical apparatus, according to an embodiment.

The method of providing information related to a location of the target object 150 via the medical apparatus may include processes of setting photographing conditions about the target object 150 (S100), acquiring current location information of the target object 150 (S200), acquiring recommended location information of the target object 150 according to set photographing conditions (S300), outputting acquired recommended location information (S400), comparing the acquired current location information and the recommended location information with each other (S500), and outputting additional information about the current location of the target object (S600).

The information related to the location according to the embodiments may include at least one of the recommended location information 15 and the additional information 17.

The recommended location information 15 according to the present embodiment may include a predetermined line, a marker, and a composite image. For example, the recommended location information 15 may include the predetermined line for representing a point where the target object 150 has to be located (for example, a right or correct position). The predetermined line may include a guide line. The line may include a solid line, a dashed line, a dashed dot line, and the like; however, the embodiments are not limited thereto.

Also, the recommended location information 15 may include a marker formed as a shadow corresponding to a portion to be photographed. For example, the marker provided when an arm is photographed may be a shadow formed as an arm. Also, the marker may be expressed in various colors, such as at least one of red, yellow, green, and blue, and in various patterns, such as diagonal line pattern or drop pattern, and the color and the pattern of the marker may be changed.

In addition, the recommended location information 15 may be provided as the composite image 30 that is generated by combining a contour line representing the right or desired posture of the target object 150 for acquiring a clear image of the target object 150 and the current posture of the target object 150. The composite image 30 according to the present embodiment may include a still image, or a moving picture, including a plurality of frames; however, the embodiments are not limited thereto.

The additional information of the present embodiment may include a predetermined message, predetermined direction information, matching rate information, and color conversion information.

For example, the additional information 17 may include a guide message about the photographing process, a guidance message or direction information for changing a posture of the target object 150, matching rate (or synchronization rate) information between the recommended location information 15 and the target object 150, and information representing a change in the color or the texture expressing the recommended location information 15; however, the embodiments are not limited thereto.

For example, the guide message about the photographing process may be a message for directing a movement of the target object 150 during the photographing process, such as "To start photographing the arm, please place your arm on a recommended location" or "photographing has finished, is next to be photographed is a leg".

Also, the guide message for changing the posture of the object may be, for example, "please lift your arm" or "please keep your legs together" so that the target object 150 moves to the recommended location.

The direction information for changing the posture of the target object 150 may refer to information including characters, numbers, and arrows for directing the target object 150 to be located on the recommended position by moving in at least one of upper, lower, left, and right directions.

Also, the matching rate information between the recommended location information 15 and the target object 150 may refer to information representing how the recommended location information 15 and the current location of the target object 150 overlap with each other or coincide with each other. For example, the matching rate may be intuitively represented by using the characters or the numbers, or may be metaphorically expressed by using a predetermined image, such as a smile image, of which a degree of the smile varies.

Also, the conversion information of the color or texture representing the recommended location information 15 may refer to, for example, information representing a change of the recommended location information 15 from yellow to green or a change of the pattern from no pattern to diagonal pattern. For example, when the recommended location information 15 and the target object 150 do not match, the recommended location information 15 may be provided as a yellow line or a marker, and when the recommended location information 15 and the target object 150 match, the color of the recommended location information 15 may be changed into green. That is, if the recommended location information 15 and the target object 150 match, the recommended location information 15 may be expressed by a green line or a marker. Also, if the recommended location information 15 and the target object 150 do not match, the recommended location information 15 is expressed as the diagonal pattern, and when the recommended location information 15 and the target object 150 match, the recommended location information 15 may be changed into a check pattern.

The medical apparatus according to the embodiment may include an X-ray photographing apparatus.

The photographing conditions according to the embodiment may include a medical apparatus selection condition for selecting the medical apparatus, and a photograph selection condition for selecting a portion to be photographed.

In addition, the photographing conditions according to the embodiment may include a condition about at least one of the location of the X-ray tube, a size of the collimator, a location of the X-ray detector, and a resolution of the image. Such photographing conditions described above may include, for example, at least one of the X-ray irradiation strength, a location of the X-ray source, a size of the collimation (for example, a size of an irradiation range that is determined by at least one of a location of the collimator and a size of the collimator), a location of the X-ray detector, and a resolution of the image.

Also, the photographing conditions according to the embodiment may be determined based on attribute information of the target object 150. The attributes of the target object 150 according to the present embodiment may include age, gender, height, weight, body shape, a portion to be photographed, and a medical history of the target object 150.

That is, at least one of the X-ray irradiation intensity, the location of the X-ray source, the size of the collimation (for example, the size of an irradiation range that is determined by at least one of a location of the collimator and a size of the collimator), the location of the X-ray detector, and a resolution of the image may be set based on at least one of the age, gender, height, weight, body shape, the portion to be photographed, and the medical history of the target object 150. For example, when the chest of the target object is to be photographed, the X-ray irradiation intensity has to vary depending on whether the target object 150 is a child or an adult. Also, the location of the X-ray source, the size of the collimation, and the location of the X-ray detector have to be adjusted according to body measurement information, such as the height and the weight of the target object 150.

Figure 4:
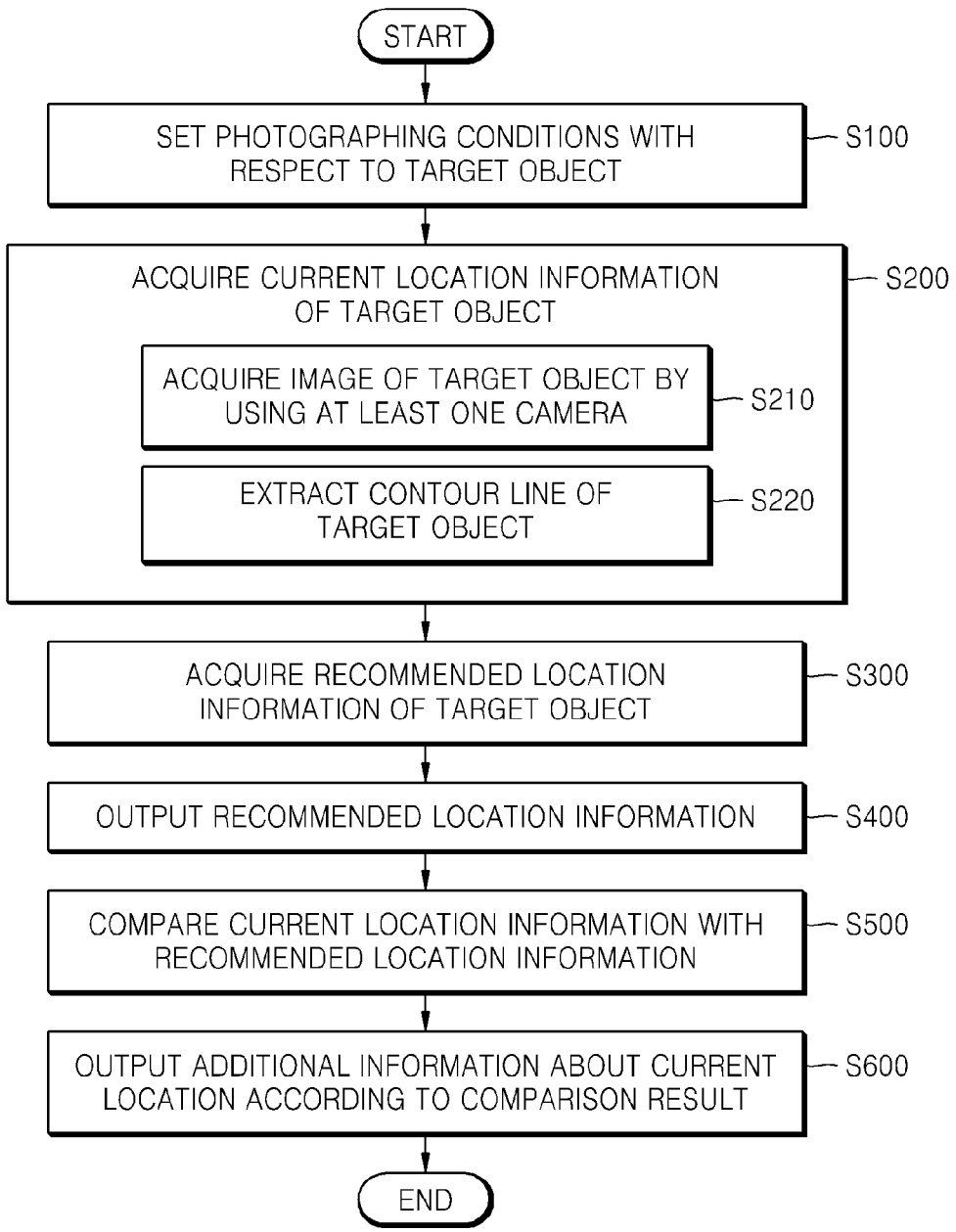
FIG. 4 is a flowchart illustrating a method of acquiring current location information of the target object, according to the embodiment.

FIG. 4 is a flowchart illustrating a method of obtaining current location information of the target object 150, according to an embodiment.

An operation of acquiring current location information of the target object 150 (S200) according to the present embodiment may include acquiring an image including the target object 150 by using at least one camera under set photographing conditions (S210), and extracting a contour line of the target object 150 from the acquired image (S220).

The current location information according to the present embodiment may include information about the contour line.

FIG. 5, including FIGS. 5A, 5B and 5C, is a diagram showing an example of acquiring the current location information of the target object 150 with a 2D camera, a stereo camera and a depth camera, according to the embodiment.

According to the embodiment, an image including the target object 150 may be acquired by using at least one camera under the photographing conditions set in operation S100 (S210). The camera according to the present embodiment may be a two-dimensional (2D) single camera 120a, a 2D stereo camera 120b, or a 3D depth camera 120c.

The 2D single camera 120a according to the present embodiment may include a general camera for photographing the target object 150. A picture or a moving picture of a subject may be acquired by the 2D single camera 120a. The subject according to the present embodiment may be the target object 150 described above.

The 2D stereo camera 120b according to the present embodiment may include a plurality of 2D single cameras 120a having the same or different specifications. For example, the 2D stereo camera 120b may include a plurality of the 2D single cameras 120a that are the same or different. A picture or a moving picture having multi-viewpoints with respect to the target object 150 may be obtained by using the 2D stereo camera 120b.

The 3D depth camera 120c according to the present embodiment may include a camera for obtaining depth information of the subject. For example, a picture or a moving picture including depth information of the target object 150 may be obtained by using the 3D depth camera 120c.

A contour line 13 of the target object 150 may be extracted from the image acquired by using the 2D single camera 120a, the 2D stereo camera 120b, or the 3D depth camera 120c (S220).

For example, the contour line 13 of the target object 150 may be extracted from the picture or the moving picture of the target object 150 that is acquired by the 2D single camera 120a. For example, the contour line 13 of the target object 150 may be extracted by using a segmentation technology used in a general image processing technology.

Also, the contour line 13 of the target object 150 may be extracted from the multi-view picture or the multi-view moving picture about the target object 140 that is obtained by using the 2D stereo camera 120b that may consist of the plurality of 2D single cameras 120a that may be the same or different. For example, depth information of the target object 150 is extracted from the multi-view picture or the moving picture, and then, the contour line 13 of the target object 150 may be obtained based on the extracted depth information.

That is, the depth information of the target object 150 with respect to each of the multi viewpoints of the image is obtained, and then, the contour line 13 of the target object 150 may be determined by using the obtained depth information. For example, the depth information may be obtained by using a difference between location information of the target object 150 or background according to one of the multi viewpoints and location information of the target object 150 or background according to another viewpoint that is different from the above viewpoint. For example, when it is assumed that the background has the largest depth information, one or more points having relatively less depth information value, which are arranged a predetermined distance ahead from the background, are connected to each other to extract the contour line 13 of the target object 150. That is, points of the target object 150 that are disposed closer to the user than the background are connected to obtain the contour line 13 of the target object 150. However, the method of obtaining the contour line 13 is not limited to the above example.

In addition, the contour line 13 of the target object 150 may be obtained from the picture or the moving picture obtained by using the 3D depth camera 120c according to the present embodiment.

For example, since the picture (or the moving picture) obtained by using the 3D depth camera 120c already includes depth information of the target object 150 or the background, the contour line 13 of the target object 150 may be obtained by using the depth information as described above. That is, points having the same or similar depth information values are connected to each other in the picture (or the moving picture) obtained by using the 3D depth camera 120c, and thus, the contour line 13 of the target object 150 may be obtained.

In addition, according to the embodiment, the contour line 13 may be emphasized. For example, the contour line 13 of the target object 150 may be represented as a dashed line, a solid line, or a dashed dot line, or the contour line 13 may be represented in a different color from the other portion of the target object 150. That is, the target object 150, except for the contour line 13, may be represented in an achromatic color, and the contour line 13 may be emphasized by using a color, such as red, yellow, or blue; however, the embodiments are not limited thereto.

Figure 6:
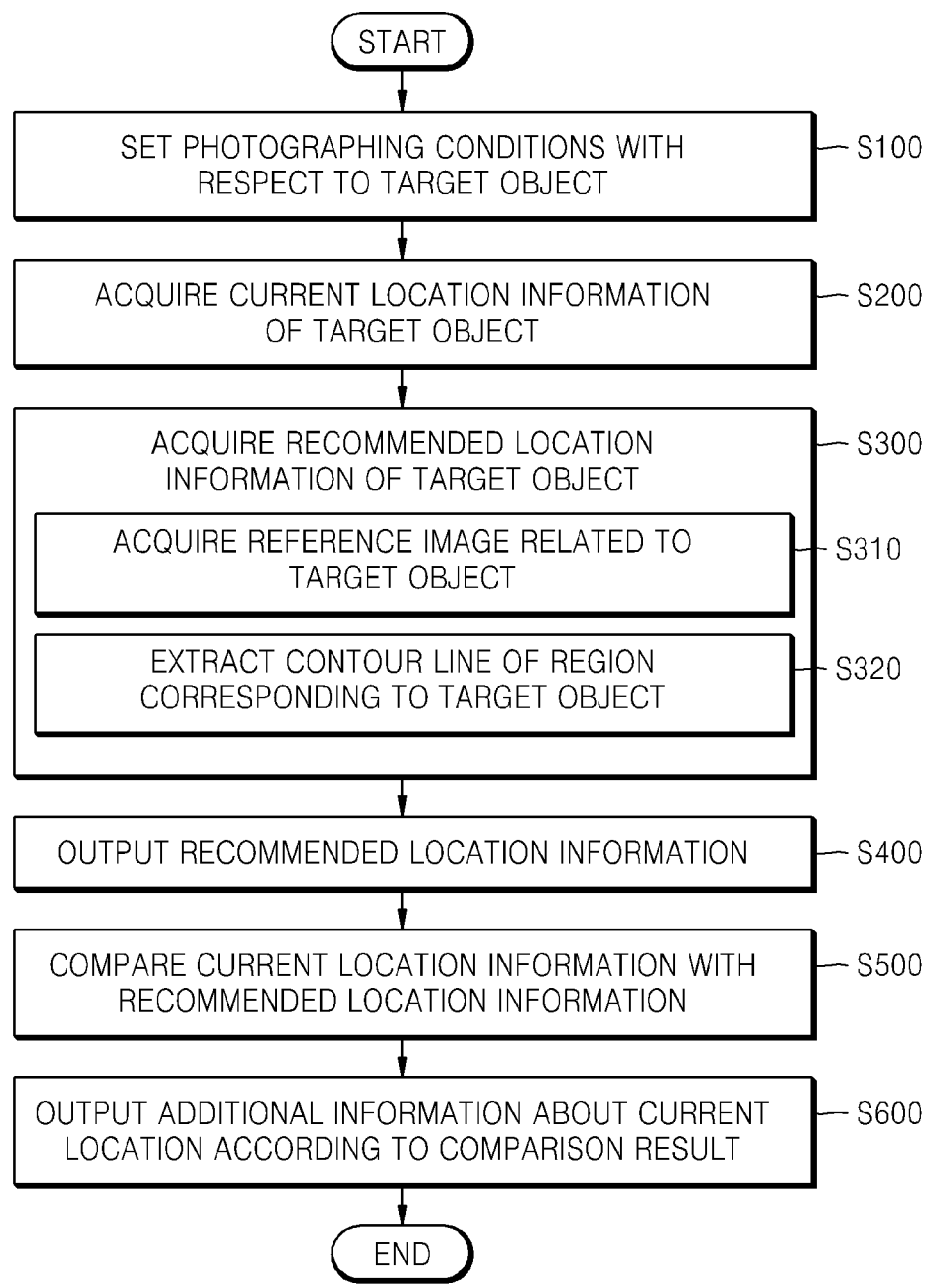
FIG. 6 is a flowchart illustrating a method of acquiring recommended location information of a target object, according to an embodiment.

FIG. 6 is a flowchart illustrating a method of obtaining recommended location information of an target object 150, according to an embodiment.

An operation of acquiring recommended location information according to the present embodiment (S300) includes acquiring a reference image relating to the target object (S310), and extracting a contour line of a region included in the acquired reference image and corresponding to the target object (S320).

The recommended location information according to the present embodiment may include information about the contour line of the extracted region, as described in detail with reference to FIG. 7.

FIG. 7 shows an example of acquiring recommended location information from a reference image 10, according to the embodiment.

The reference image 10 of the target object according to the present embodiment may be determined in advance statistically according to the portion to be photographed of the target object and stored in advance in a database. For example, a predetermined element found in chest X-ray images with respect to a plurality of different object bodies (for example, the number of ribs included in the image, and the location of a diaphragm) is extracted, and a plurality of elements are defined as common features based on the number of occurrences from the plurality of chest X-ray images with respect to the plurality of different object bodies. In addition, a chest X-ray image of a predetermined target object having the common features may be determined as the reference image and stored.

Also, the reference image 10 according to the present embodiment may be selected based on features of the target object to be photographed from among the images of the plurality of object bodies, which are stored in advance. The features of the target object may include age, gender, height, weight, body shape, a portion to be photographed, and a medical history of the target object.

That is, the reference image may be selected based on at least one of the age, gender, height, weight, body shape, the portion to be photographed, and the medical history of the target object from among the images with respect to the plurality of object bodies stored in advance. For example, the reference image of a child's chest and the reference image of an adult's chest may be selected differently from among the stored images with respect to the plurality of object bodies.

Also, the reference image according to the present embodiment may be an image having the highest clarity of the portion to be photographed under the set photographing conditions. As described above, in order to accurately diagnose the disease of the target object, a clear image of the target object has to be obtained. Therefore, according to the present embodiment, the reference image may be the image having the highest clarity from among the images stored in advance.

As shown in FIG. 7, the reference image 10 according to the portion to be photographed of the target object may be acquired. A contour line 12 of a region corresponding to the target object (or the photographed portion of the target object) may be extracted from the acquired reference image 10. The recommended location information 15 of the target object may be determined in advance by using the extracted contour line 12.

For example, the recommended location information 15 may be determined by using at least one of the location and size of the contour line 12 in the reference image 10. That is, the location of the recommended location information 15 may be determined to correspond to the location of the contour line 12 in the reference image 10. Also, the size of the recommended location information 15 may be determined in consideration of the size (or area) ratio of the contour line 12 area with respect to the size (or entire area) of the reference image 10.

Figure 8:
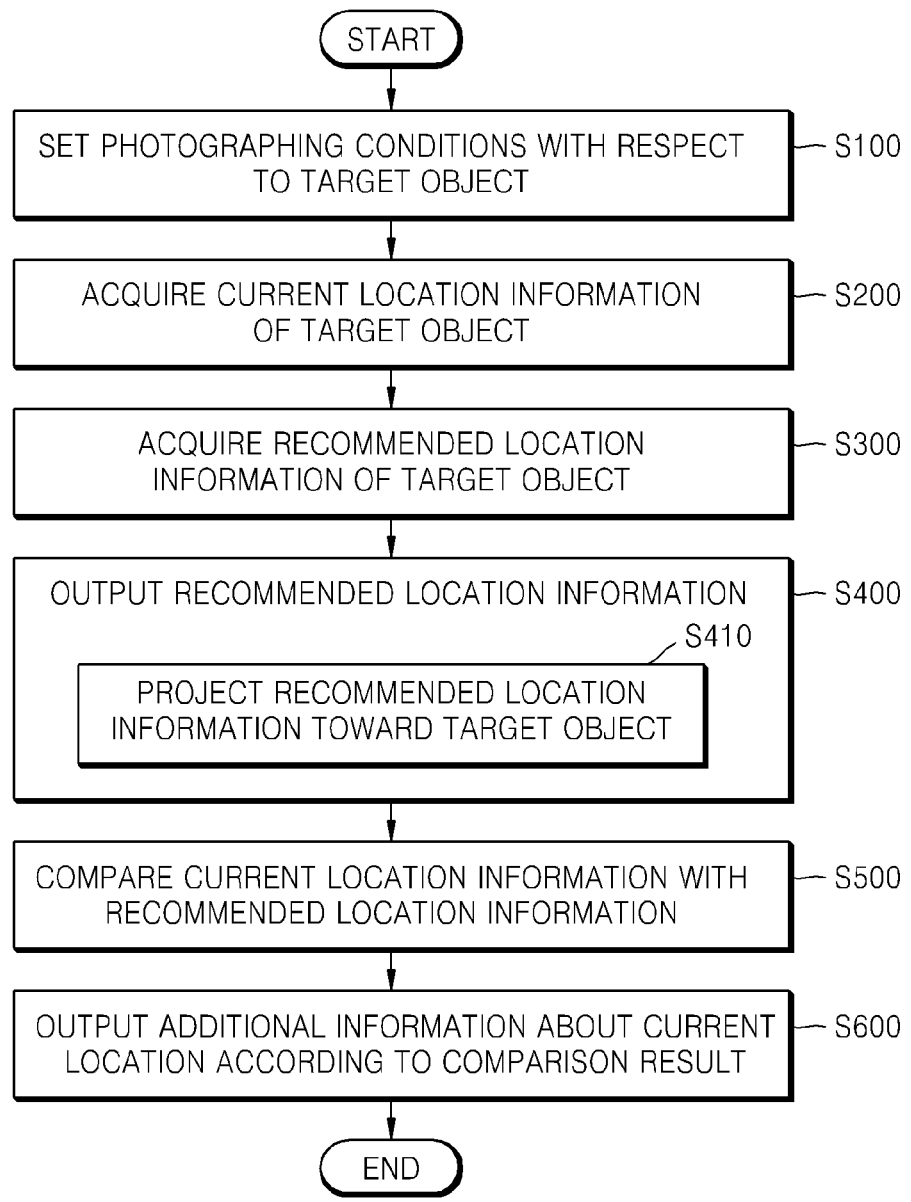
FIG. 8 is a flowchart illustrating a method of providing recommended location information, according to an embodiment.

FIG. 8 is a flowchart illustrating a method of providing recommended location information, according to an embodiment.

An operation of outputting the recommended location information acquired according to the embodiment (S400) may include projecting the recommended location information onto the target object (S410). Operation S410 will be described with reference to FIG. 9 below.

Figure 9:
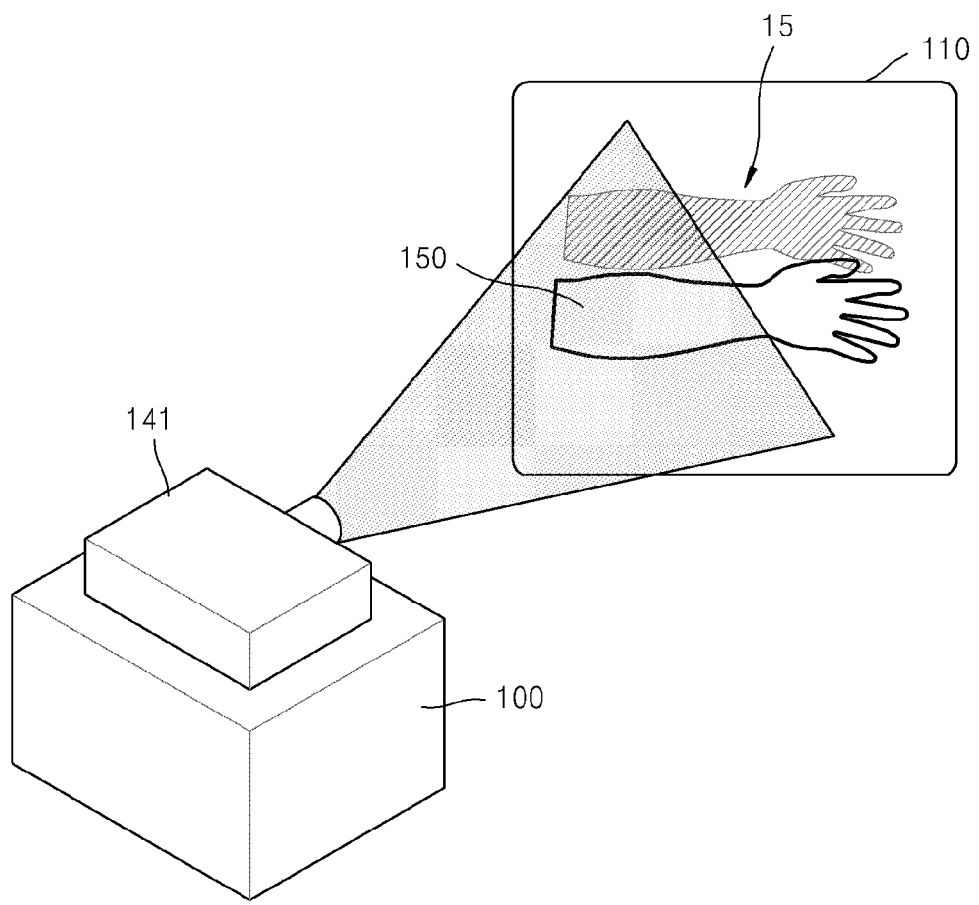
FIG. 9 is a diagram showing an example of providing recommended location information, according to an embodiment.

FIG. 9 is a diagram showing an example of providing recommended location information, according to the embodiment.

The output of the recommended location information 15 according to the embodiment may include a projection toward the target object via a projector 141. For example, the recommended location information 15 may be directly projected toward the X-ray detector 110 via the projector 141 disposed at a side of the X-ray source 100. Also, the recommended location information 15 may be directly projected onto the target object 150 located on the X-ray detector 110 via the projector 141 disposed at the side of the X-ray source 100.

FIG. 10 is a flowchart illustrating a method of comparing current location information and the recommended location information, according to an embodiment.

The operation of comparing the current location information and the recommended location information (S500) may include determining the similarity between the current location information of the target object 150 and the recommended location information (S510).

The similarity between the current location information of the object 150 and the recommended location information 15 may be determined by using a model-based matching method.

FIGS. 11A and 11B are diagrams showing an exemplary method of determining similarity, according to an embodiment.

As shown in FIG. 11A, a contour line of the target object 150 on the current location is extracted from the image 11 obtained by using the 2D single camera 120*a* or the like, and the similarity may be determined according to an overlapping degree between the extracted contour line 13 of the target object and the recommended location information 15.

For example, if the contour line 13 of the target object 150 and the recommended location information 15 do not overlap with each other at all, the similarity may be represented as 0, and thus, it may be determined that the contour line 13 of the target object and the recommended location information 15 are not similar to each other. That is, it may be determined that the target object 150 is not located to correspond to the recommended location information 15. In this case, the target object 150 has to move to overlap with the recommended location information 15. For example, the target object 150 may change his/her posture to correspond to the recommended location information 15.

On the other hand, if the contour line 13 of the target object 150 and the recommended location information 15 completely overlap with each other, the similarity may be 1, and it may be determined that locations of the contour line 13 of the target object and the recommended location information 15 coincide with each other. For example, since the target object 150 has a posture that corresponds to the recommended location information 15, the target object 150 has to maintain the posture during the photographing process.

Also, as shown in FIGS. 11B and 11O, depth information of the target object is extracted from an image obtained by using the 2D stereo camera 120b (for example, an image 14) or from an image obtained by using the 3D depth camera 120c (for example, an image 16), and a contour line of the target object is obtained based on the depth information. Then, the similarity between the current location information and the recommended location information may be determined according to an overlapping degree between the contour line and the recommended location information 15.

FIGS. 12A through 12D are diagrams showing examples of providing additional information, according to an embodiment.

An operation of outputting additional information about the current location of the target object 150 according to a result of comparing the current location information and the recommended location information (S600) may include outputting at least one of correction information of the location of the target object 150 and information representing the similarity.

The additional information 17 according to the present embodiment may be output as at least one of text, sound, and an image.

As described above, when the recommended location information 15 and the target object 150 completely overlap each other, the similarity may be 1, and it may be determined that the target object 150 is located to correspond to the recommended location information 15. In this case, the target object 150 (or the contour line of the target object 150) and the recommended location information 15 coincide with each other. That is, the target object 150 has a posture corresponding to the recommended location information 15; the target object 150 does not need to change his/her posture.

Therefore, when the target object 150 has the posture suitable for the recommended location, as shown in FIG. 12A, a predetermined notification message may be output as the additional information 17. For example, a notification message, such as "exact", may be output as the information regarding the correction of the location of the target object 150.

Also, as shown in FIG. 12B, a predetermined image may be used to represent whether the target object 150 is located at the recommended location. For example, when the target object 150 is located to correspond to the recommended location information 15 (for example, when the target object 150 and the recommended location information 15 completely overlap with each other), a smile character having the largest smile may be output as the additional information 17. That is, as the target object 150 and the recommended location information 15 gradually overlap with each other, the additional information 17 may be output as the character whose smile gets bigger.

Also, a predetermined image including an icon that changes when the target object 150 and the recommended location information 15 gradually overlap with each other may be output as the additional information 17. For example, when the target object 150 and the recommended location information 15 do not overlap with each other, an X-shaped icon (or image) is output. When the target object 150 and the recommended location information 15 overlap with each other, an O-shaped icon (or image) may be output.

Also, the similarity (or concordance rate) between the target object 150 and the recommended location information 15 may be expressed by a predetermined number. For example, when the target object 150 and the recommended location information 15 do not coincide with each other at all (for example, the target object 150 and the recommended location information 15 do not overlap with each other), a predetermined character or number such as "similarity 0%" may be output as the additional information 17. Also, if the target object 150 and the recommended location information 15 coincide with each other, a predetermined character or number such as "concordance rate 100%" may be output as the additional information 17.

The output of the additional information 17 according to the present embodiment may include projecting the additional information 17 onto the target object 150 by using the projector 141. Also, the output of the additional information 17 may include projecting the additional information 17 toward the X-ray detector 110 via the projector 141.

According to an embodiment, as shown in FIG. 12C, when the target object 150 does not overlap with the recommended location information 15, information regarding location correction may be output as the additional information 17. For example, a message, such as "move your right arm upward" may be provided as the information regarding the location correction. Also, when the target object 150 moves and overlaps with the recommended location information 15, a message such as "exact, please do not move" may be output as the additional information 17.

In addition, when the target object 150 moves and overlaps with the recommended location information 15, the change in the color or texture of the recommended location information 15 may be output as the additional information 17. For example, as described above, when the target object 150 moves and overlaps with the recommended location information 15, the pattern of the recommended location information 15 may be changed from the diagonal pattern to the check pattern.

Also, according to the embodiment, as shown in FIG. 12D, when the target object 150 does not overlap with the recommended location information 15, information regarding the location correction may be output as the additional information 17. For example, a direction (for example, at least one of a direction or an angle) or a distance (for example, a few centimeters (cm)) that the target object 150 has to move in order to overlap with the recommended location information 15 may be provided as the information regarding the location correction by using an arrow or numbers.

Also, the direction or the distance that the target object 150 has to move in order to overlap with the recommended location information 15 may be represented as a predetermined image, such as a character, as shown in FIG. 12D. Such an image may include an animation image or a moving picture. Also, when the target object 150 overlaps with the recommended location information 15, the image, such as a character having the biggest smile, may be output as the additional information 17.

Also, the additional information 17 may be provided to the target object 150 as a sound such as a voice via a speaker. For example, the additional information 17, for example, the message such as "move your arm upward" or "exact, please do not move" may be provided to the target object 150 as a voice via the speaker.

Figure 13:
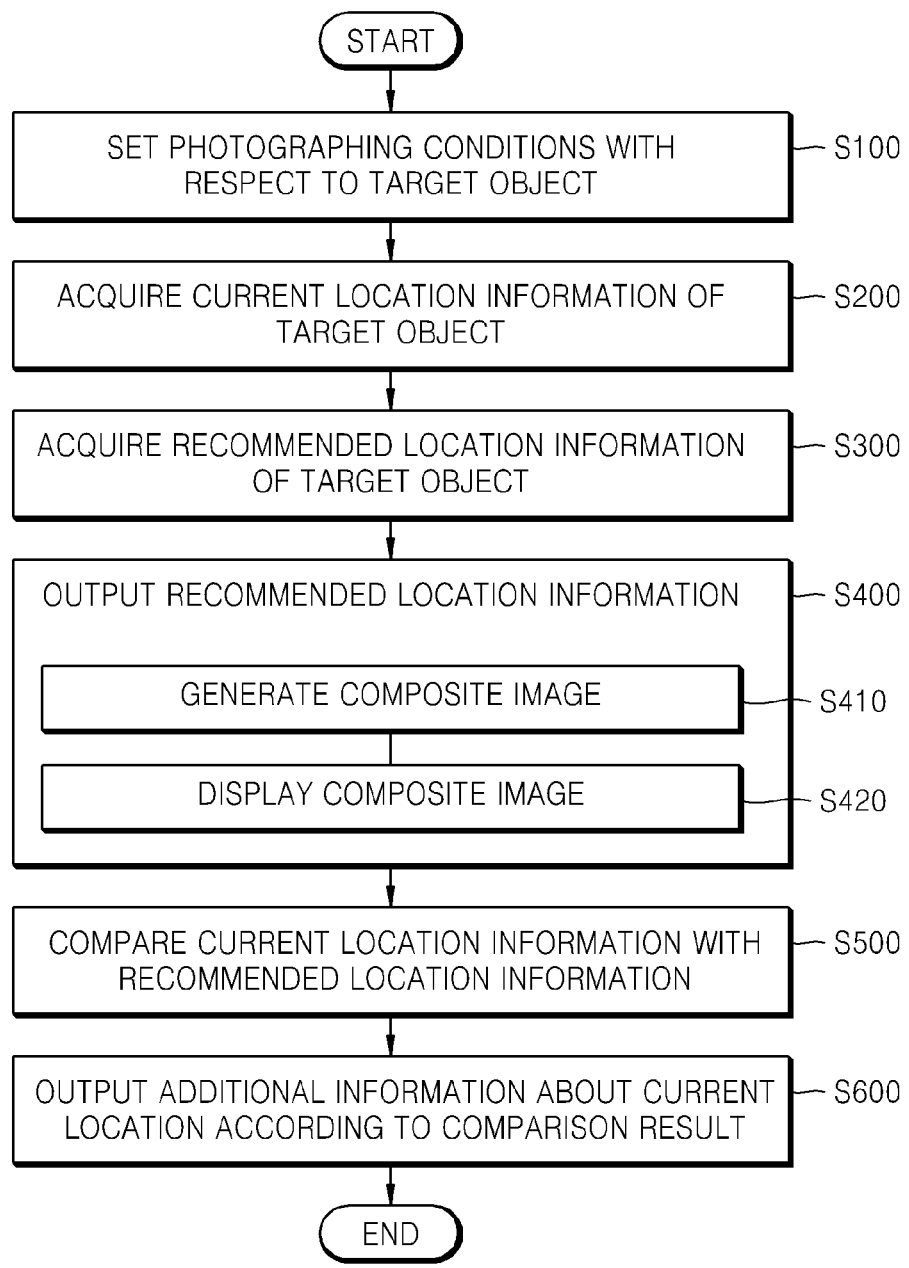
FIG. 13 is a flowchart illustrating a method of providing recommended location information, according to another embodiment.

FIG. 13 is a flowchart illustrating a method of providing recommended location information, according to another embodiment.

An operation of outputting acquired recommended location information (S400) according to the present embodiment may include generating a composite image by overlapping a contour line with an acquired image (S410), and displaying the generated composite image (S420).

According to the present embodiment, for example, the contour line extracted from the reference image 10 corresponding to the portion of the target object 150 to be photographed is combined with the image of the target object 150 that is acquired by the camera to generate a composite image (S410), and the generated composite image is displayed (S420). Thus, the recommended location information 15 may be provided to the target object 150, as described below with reference to FIG. 14.

Figure 14:
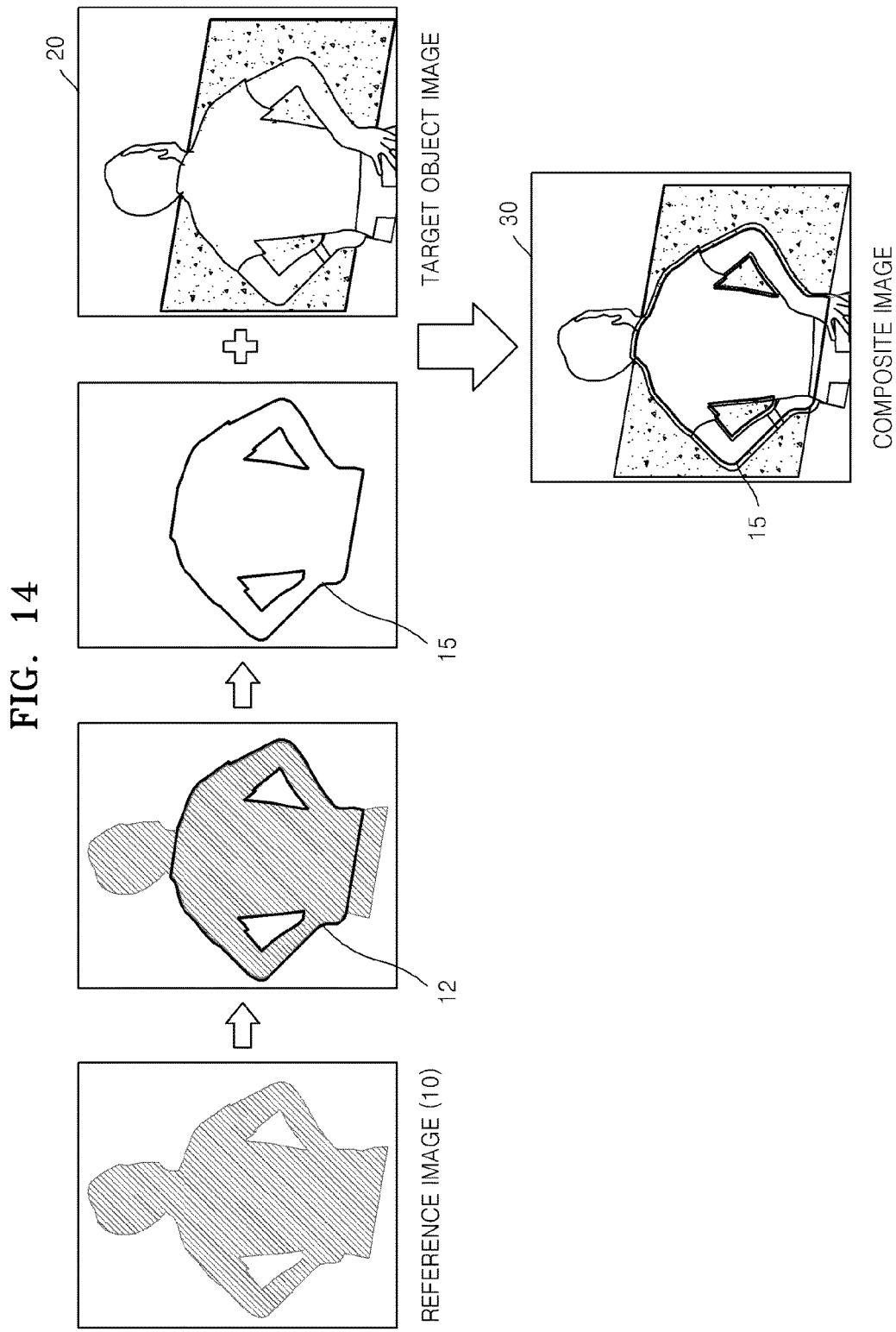
FIG. 14 is a diagram showing an example of providing recommended location information, according to an embodiment.

FIG. 14 is a diagram showing an example of providing recommended location information, according to the present embodiment.

According to the present embodiment, a contour line 12 may be extracted from the reference image 10, corresponding to the portion of the target object 150 to be photographed. For example, when the chest of the target object 150 is to be photographed, the reference image 10 of the chest is acquired, and the contour line 12 corresponding to the target object 150 may be extracted from the reference image 10. The contour line 12 may be included in the recommended location information 15. The method of extracting the contour line 12 is described above with reference to FIGS. 6 and 7.

Also, an image 20 of the target object 150 may be acquired by using at least one camera. The acquisition of the image 20 of the target object 150 is described above with reference to FIGS. 4 and 5.

According to the present embodiment, the contour line 12 extracted from the reference image 10 and the image 20 of the target object 150 may be combined to generate a composite image 30. The composite image 30 may be provided to the target object 150. For example, the composite image 30 may be displayed on a device having a display function.

The target object 150 may recognize how his/her posture is different from the recommended location information 15 by using the composite image 30, and may correct his/her posture.

Figure 15:
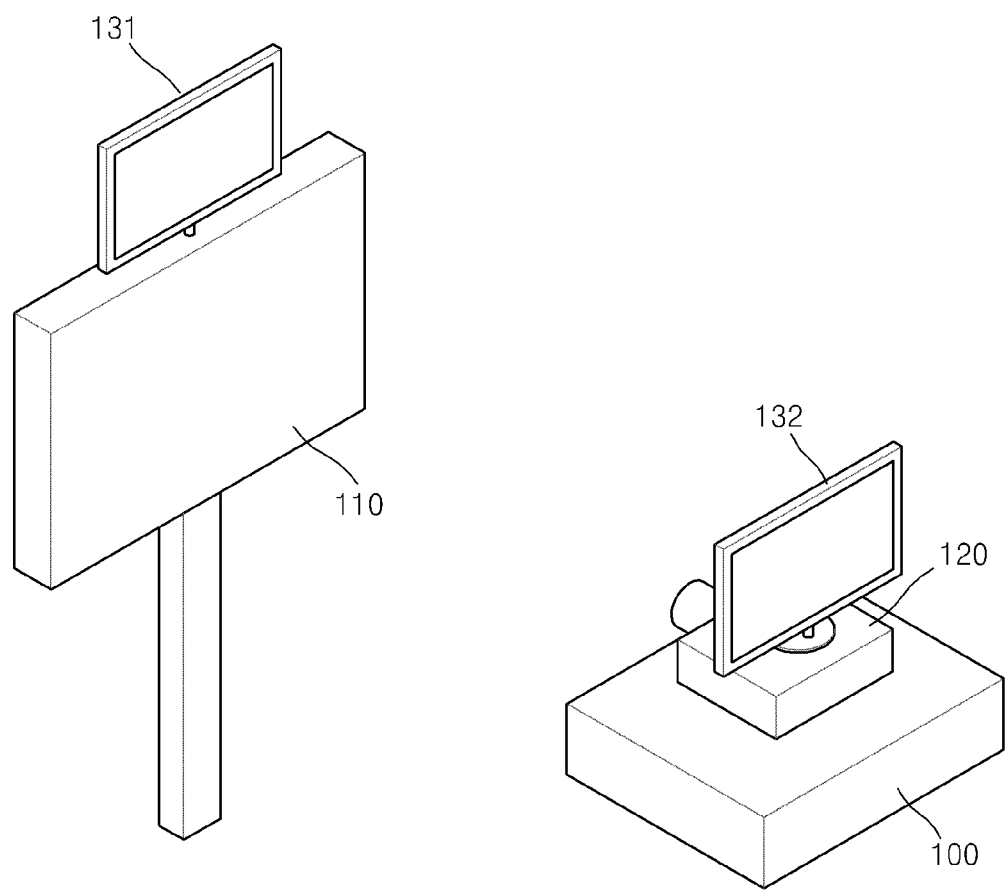
FIG. 15 is a diagram showing an example of providing recommended location information and additional information by using a liquid crystal display (LCD) panel, according to an embodiment.

FIG. 15 is a diagram showing an example of providing recommended location information and additional information by using an LCD panel, according to an embodiment of the present embodiment.

The target object 150 is located between the X-ray source 100 and the X-ray detector 110, and an X-ray image of the target object 150 may be obtained. As described above, the target object 150 has to be guided to a right position in order to acquire an accurate X-ray image of the target object 150. The guidance may be performed by providing information about the recommended location (for example, a guide line) when photographing the target object 150, and as shown in FIG. 15, the recommended location information 15 may be provided to the target object 150 by using a predetermined camera 120 and an LCD panel 131/132.

The camera 120 for obtaining the image of the target object 150 according to the present embodiment may be located at a side of the X-ray source 100. For example, the camera 120 may be located on a fixed axis or a supporting axis of the X-ray source 100; however, the embodiments are not limited thereto.

Since the camera 120 is located on the fixed axis or the supporting axis of the X-ray source 100, the image of the target object 150 may be easily obtained without exposing the target object 150 to radiation. For example, when the target object 150 is photographed by the camera 120, current location information representing a current status or a current position of the target object 150 may be obtained.

Also, an LCD panel 131 or 132 for displaying the recommended location information may be located on at least one of the X-ray source 100 and the X-ray detector 110.

For example, the LCD panel 131 may be located on a fixed axis or a supporting axis of the X-ray detector 110. Also, the LCD panel 131 may be located on a wall surface of the examination room. That is, the LCD panel 131 may be located on the fixed axis or the supporting axis of the X-ray detector 110 or on the wall surface of the examination room in order to provide the target object 150 with the recommended location information when a rear portion (for example, the back) of the target object 150 is photographed.

Also, the LCD panel 132 may be located on the fixing axis or the supporting axis of the X-ray source 100. That is, the LCD panel 132 may be located on the fixing axis or the supporting axis of the X-ray source 100 within a viewing range of the target object 150 so that the target object 150 may easily identify the recommended location information when a front portion (for example, the chest) of the target object 150 is photographed.

In addition, LCD panels 131 and 132 may be located respectively on the fixing axis or the supporting axis of the X-ray source 100 and the X-ray detector 110, and at least one of the LCD panels 131 and 132 may be used to provide the recommended location information 15 according to a control input of the user.

Figure 16A:
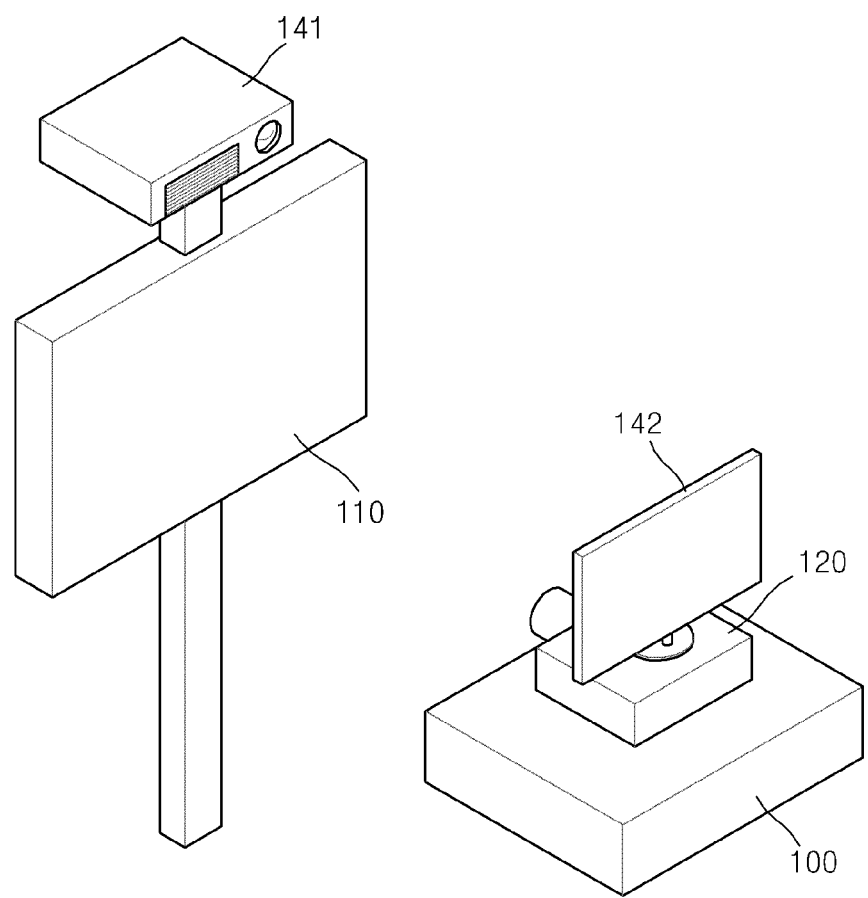
FIGS. 16A and 16B are diagrams showing examples of providing at least one of recommended location information and additional information by using a projector, according to an embodiment.
Figure 16B:
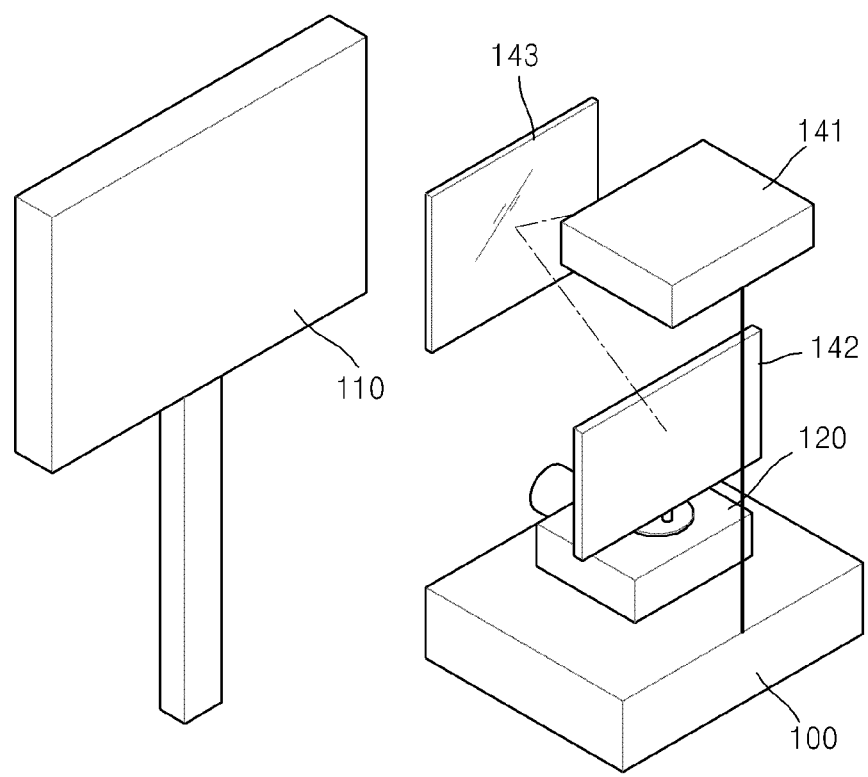

FIGS. 16A and 16B are diagrams showing examples of providing the recommended location information and the additional information by using the projector 141, according to an embodiment the present embodiment.

According to the present embodiment, the projector 141 may be used to provide the recommended location information 15 for photographing the target object 150.

The projector 141 for providing the target object 150 with the recommended location information 15 may be located at a side of the X-ray detector 110. For example, the projector 141 may be located on the fixing axis or the supporting axis of the X-ray detector 110; however, the embodiments are not limited thereto.

Also, a predetermined screen 142 for displaying the image projected from the projector 141 located at the X-ray detector 110 may be located on the fixing axis or the supporting axis of the X-ray source 100.

For example, the projector 141 may be located on the fixing axis or the supporting axis of the X-ray detector 110, and the screen 142 may be located on the fixing axis or the supporting axis of the X-ray source 100, and thus, the same effect as that of the above case in which the recommended location information is provided by using the LCD panels may be obtained. That is, at least one of the recommended location information and the additional information projected from the projector 141 may be provided to the target object 150 via the screen 142, and the target object 150 may correct his/her posture by using at least one of the recommended location information and the additional information. In addition, the user may easily determine whether the photographing has to proceed (for example, whether to perform the photographing or whether to correct the posture of the target object 150), and a possibility of obtaining a clear image of the target object 150 may be improved.

Also, according to the present embodiment, the projector 141 and the screen 142 may be located on the fixing axis or the supporting axis of the X-ray source 100. In this case where the projector 141 and the screen 142 are located on a side of the X-ray source 100, an image transfer unit 143 may be used to project the image from the projector 141 onto the screen 142. For example, the image transfer unit 143 may include a reflector, such as at least one mirror. The image transfer unit 143 according to the present embodiment may be moveable in a predetermined direction or angle, as described later with reference to FIG. 18.

For example, as shown in FIG. 16B, the image projected from the projector 141 may be displayed on the screen 142 via the image transfer unit 143. That is, when the front part (for example, the chest) of the target object 150 is photographed, the recommended location information 15 may be provided to the target object 150 via the projector 141, the screen 142, and the image transfer unit 143 located at a side of the X-ray source 100, and the target object 150 may correct his/her posture by using the recommended location information.

Figure 17A:
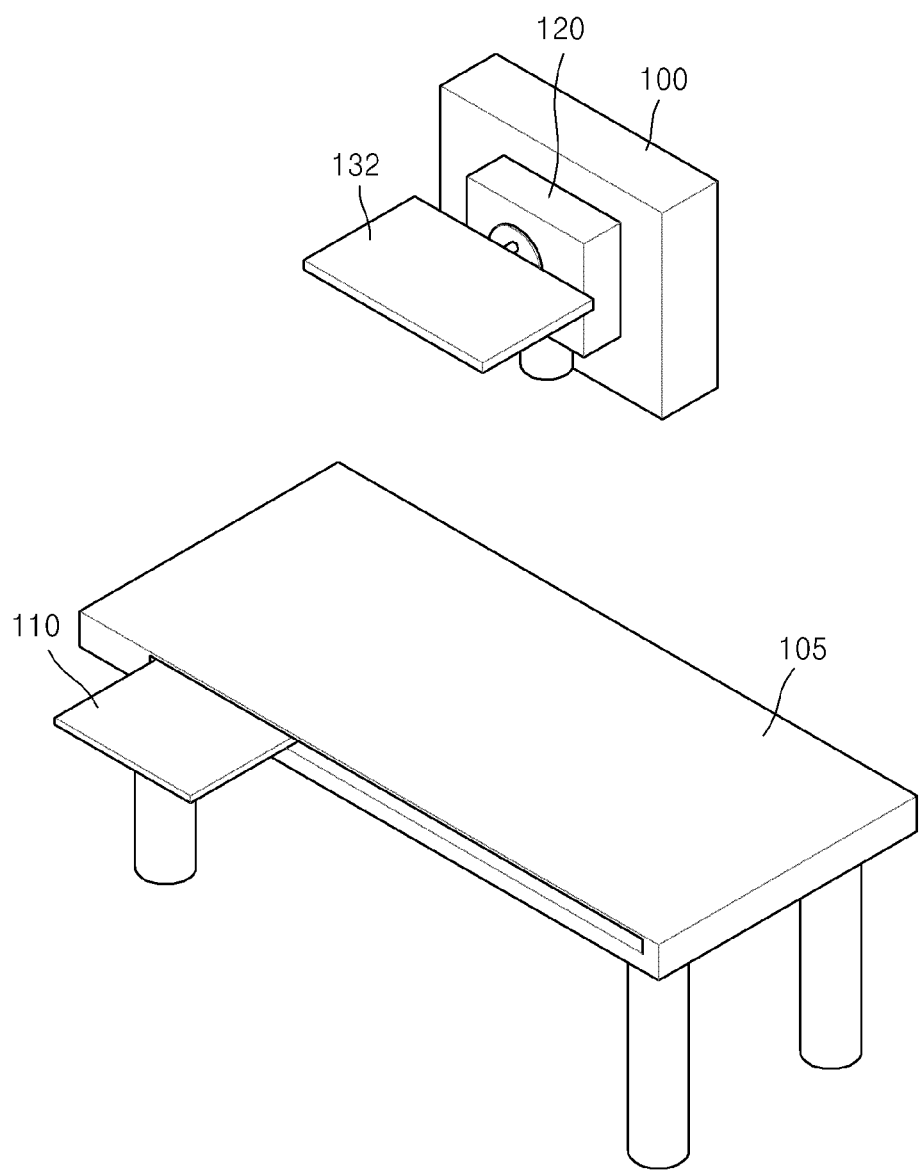
FIGS. 17A and 17B are diagrams showing examples of providing recommended location information and additional information by using an LCD panel or a projector, when a target object located on a table is photographed, according to an embodiment.
Figure 17B:
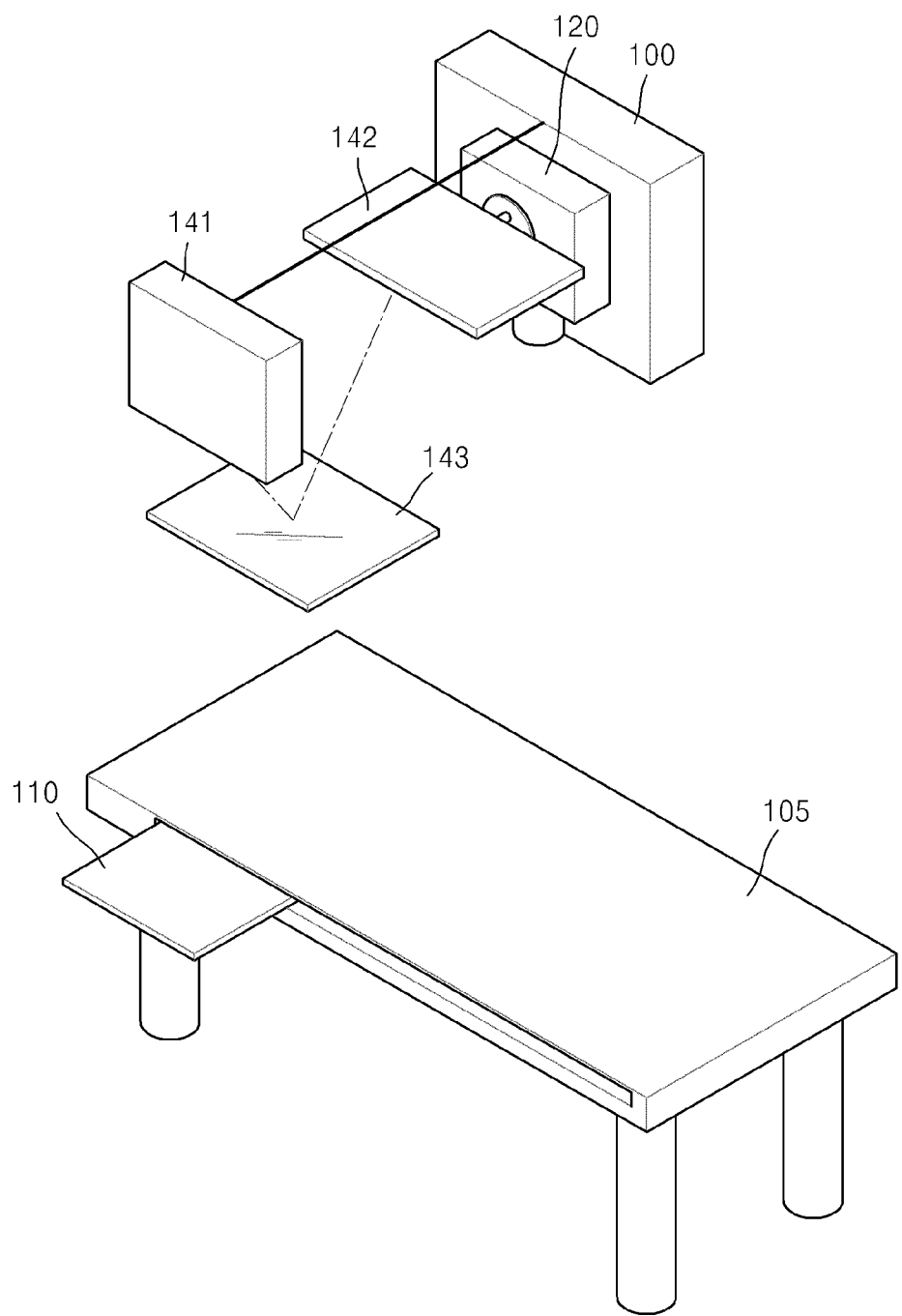

FIGS. 17A and 17B are diagrams showing examples of providing the recommended location information and the additional information by using the LCD panel 132 or the projector 141 when the target object 150 located on a table 105 is photographed, according to an embodiment.

According to the present embodiment, the target object 150 may be located on the table 105 between the X-ray source 100 and the X-ray detector 110 to acquire the X-ray image of the target object 150. For example, the case where the target object 150 is located on the table 105 may include a case where the target object 150 lies on the table 105 (decubitus) when the photographing is performed.

Similar to the above description, the LCD panel 132 for providing at least one of the recommended location information 15 and the additional information 17 may be located at a side of the X-ray source 100; however, the embodiments are not limited thereto. The LCD panel 132 may be located on the wall surface (for example, the ceiling) in the examination room. That is, the LCD panel 132 may be located on the fixing axis or the supporting axis of the X-ray source 100 or on the wall surface, such as the ceiling, in the examination room within a viewing angle range of the target object 150 so that the target object 150 may easily recognize at least one of the recommended location information 15 and the additional information 17 when the front part of the target object 150 (for example, the chest) located on the table 105 is photographed.

Also, the projector 141 or the screen 142 may be used to provide the target object 150 with at least one of the recommended location information 15 and the additional information 17.

For example, the projector 141 and the screen 142 may be located on the fixing axis or the supporting axis of the X-ray source 100. Also, the projector 141 may be located at the wall surface, such as the ceiling of the examination room.

The image transfer unit 143 may be used to project the image from the projector 141 located at the side of the X-ray source 100 to the screen 142 located at the side of the X-ray source 100. For example, the image transfer unit 143 may include a reflector, such as at least one mirror.

For example, as shown in FIG. 17B, the image projected from the projector 141 may be displayed on the screen 142 via the image transfer unit 143. The image transfer unit 143 according to the present embodiment may move in a predetermined direction or angle, as described later with reference to FIGS. 18A and 18B.

For example, when the front part of the target object 150 is photographed, the recommended location information 15 may be provided to the target object 150 via the projector 141, the screen 142, and the image transfer unit 143 that are all located on the side of the X-ray source 100, and the target object 150 may recognize the recommended location information in a comfortable status and correct his/her posture by using the recommended location information.

Figure 18A:
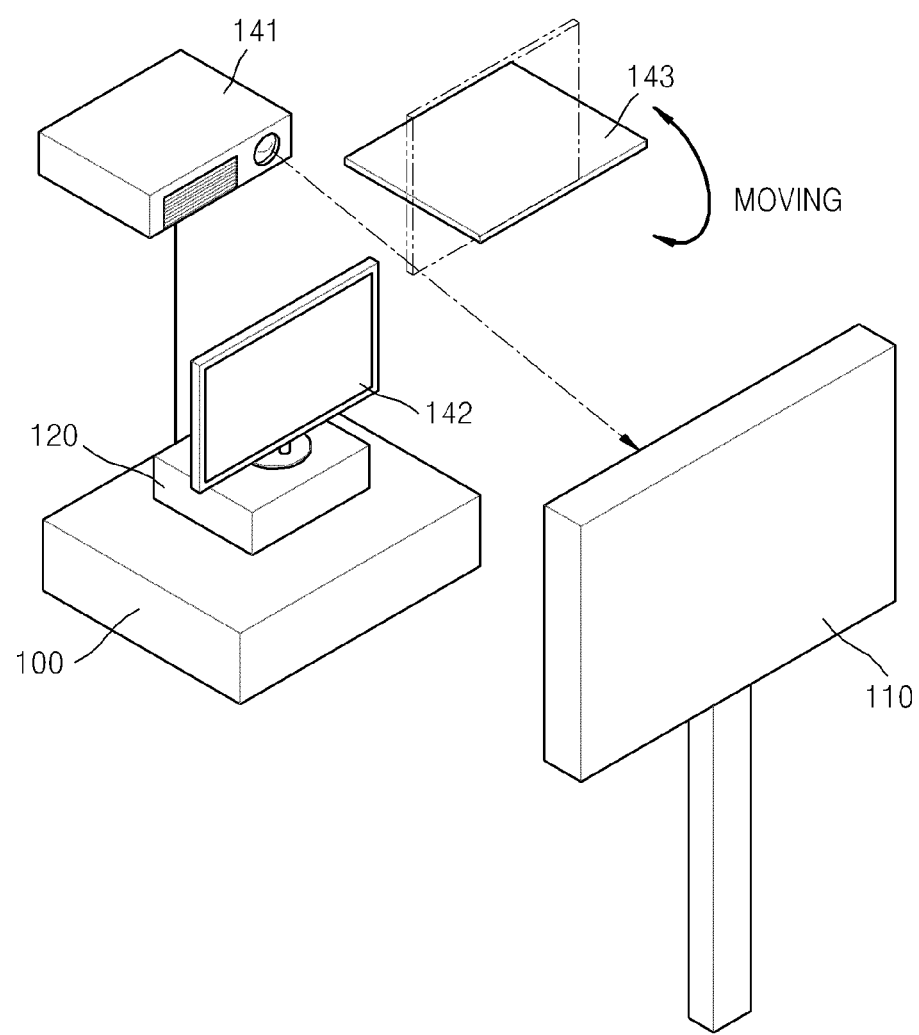
FIGS. 18A and 18B are diagrams showing examples of providing recommended location information and additional information by using the projector, according to another embodiment.
Figure 18B:
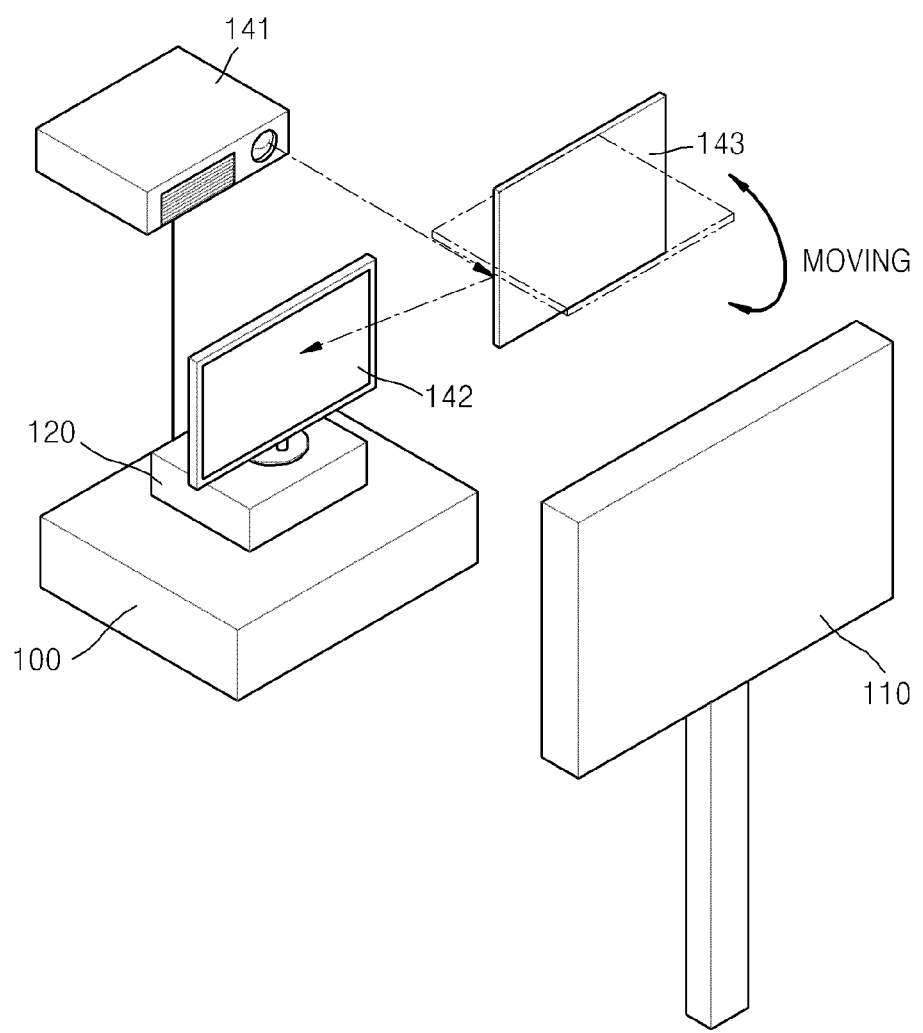

FIGS. 18A and 18B are diagrams showing examples of providing at least one of recommended location information and additional information by using the projector 141, according to another embodiment.

As shown in FIG. 18A, the projector 141, the screen 142, and the image transfer unit 143 may be located at the side of the X-ray source 100. The image transfer unit 143 according to the present embodiment may move in a predetermined direction or angle.

Referring back to FIG. 9, FIG. 9 shows an example in which the recommended location information 15 is directly projected onto the target object 150. The above direct projection may be achieved by moving the image transfer unit 143 that is moveable, as described with reference to FIG. 18. For example, by opening the image transfer unit 143, the image projected from the projector 141 may be directly projected to the X-ray detector 110.

Also, according to the present embodiment, when the image transfer unit 143 that is moveable is moved, the recommended location information may be provided to the target object 150 through the screen 142. For example, according to the embodiment, the image projected from the projector 141 is reflected by the image transfer unit 143 so that the image may be displayed on the screen 142. That is, the same effect as that of using the LCD panel 132 may be obtained by using the projector 141, the image transfer unit 143, and the screen 142.

Figure 19A:
FIGS. 19A and 19B are diagrams showing examples of providing recommended location information and additional information, according to another embodiment.
Figure 19B:
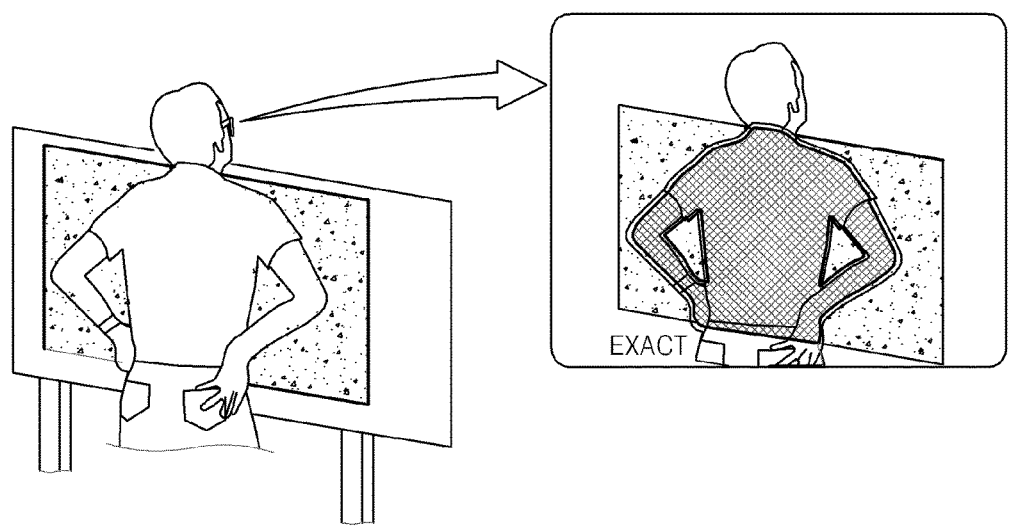

FIGS. 19A and 19B are diagrams showing examples of providing recommended location information and additional information, according to another embodiment.

The recommended location information according to the present embodiment may be provided via a wearable device 180. For example, the wearable device 180 may include augmented reality glasses, and a head-mount display, as shown in FIG. 19A.

For example, in a preparing process, the target object 150 may wear the wearable device 180. The target object 150 may receive at least one of the recommended location information 15 and the additional information 17 via the wearable device 180.

As shown in FIG. 19B, the target object 150, the rear part of which is to be photographed, wears the wearable device 180 and may be located at the side of the X-ray detector 110. As described above, at least one of the recommended location information 15 and the additional information 17 that may be included in the composite image may be provided to the target object 150 via the wearable device 180. That is, at least one of the recommended location information 15 and the additional information 17 may be displayed on the wearable device 180 that the target object 150 wears.

Figure 20:
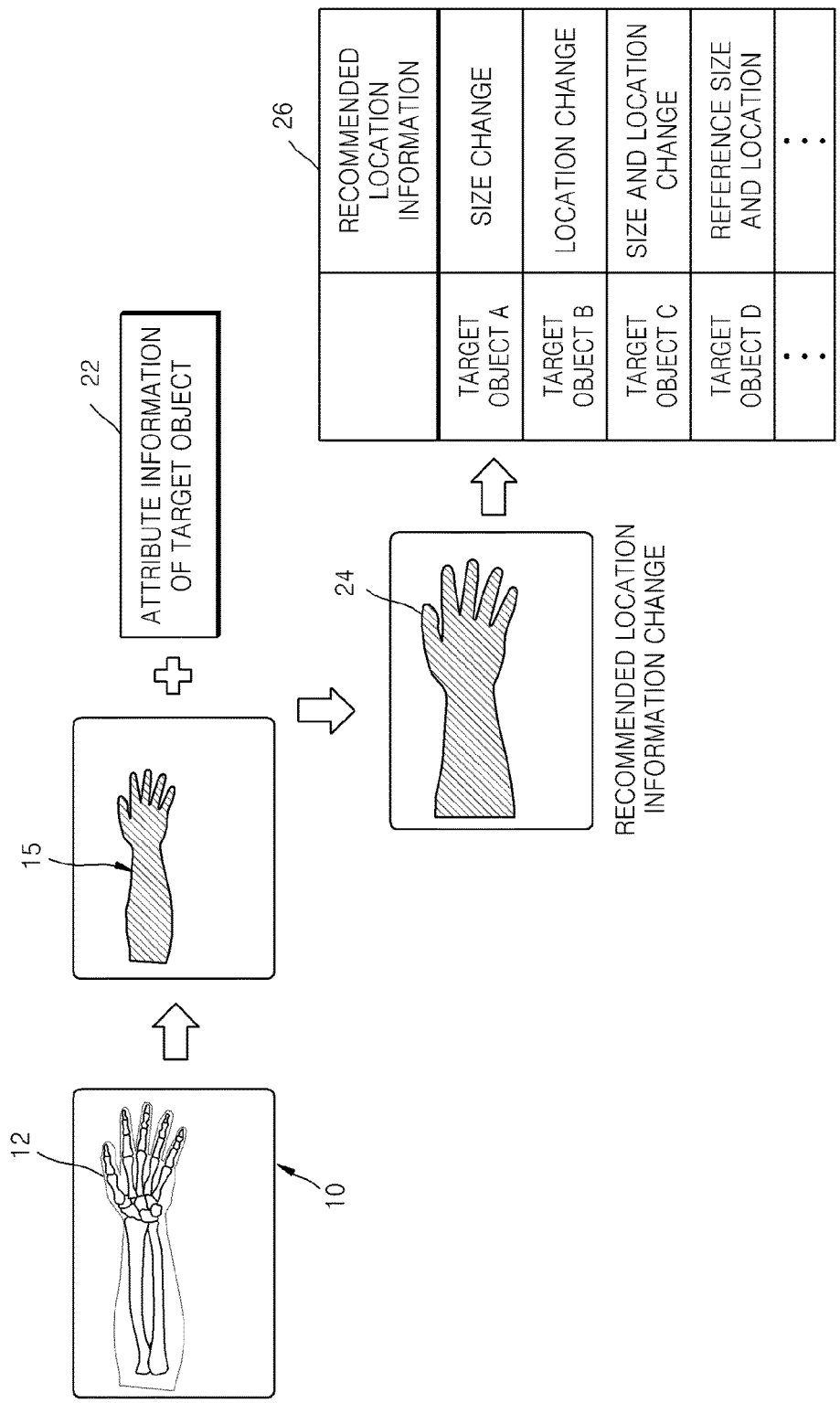
FIG. 20 is a diagram showing an example of editing or storing recommended location information, according to an embodiment.

FIG. 20 is a diagram showing an example of editing or storing recommended location information, according to an embodiment.

The recommended location information 15 according to the present embodiment may be variable according to attribute information of the target object 150. Also, the recommended location information 15 that is variable may be stored to correspond to the attribute information of the target object 150.

For example, the recommended location information 15 that is acquired based on the contour line 12 corresponding to the target object 150 in the reference image 10 may be changed according to attribute information 22 of the target object 150.

That is, with respect to a target object A who has a greater size (for example, volume) than that of a general target object (for example, a target object D), a size of a guide line representing the recommended location may be increased. For example, the guide line that is a type of the recommended location information 15 for the general target object D may be expanded to be suitable for the target object A (24).

Similarly, a location of the recommended location information 15 may be variable, as well as the size thereof. For example, the location of the recommended location information 15 may vary depending on the target object 150. If an target object B has a greater height than that of the target object D, the recommended location information with respect to the target object B has to be provided at a location higher than the recommended location information with respect to the target object D. In addition, if an target object C is shorter than the target object D, the recommended location information with respect to the target object C has to be provided at a location that is lower than the recommended location information with respect to the target object D. That is, the location where the recommended location information may be changed based on the attribute including body measuring information of the target object.

Also, the recommended location information may have a bigger or smaller size than the reference recommended location information (for example, the recommended location information 15) according to the attribute of the target object, and may move in at least one of upper, lower, left, and right directions. For example, with respect to the target object (for example, target object C) having a greater volume and less height than the general target object (for example, target object D), the guide line representing the recommended location may be expanded and the recommended location information may be provided at a lower location than the reference recommended location information.

The recommended location information that is variable may be stored as a table 26 corresponding to the attribute information of the target object; however, the embodiments are not limited thereto. Otherwise, the recommended location information may be stored as the table 26 corresponding to identifiers of the target object. The identifier of the target object may include an exclusive code consisting of letters or numbers. The attribute of the target object according to the present embodiment may include age, gender, height, weight, body shape, a portion to be photographed, and a medical history of the target object, as described above.

For example, a size of the recommended location information may be changed based on the attribute information of an target object A, and the changed recommended location information may be stored with the attribute information of the target object A. In addition, the location where the recommended location information may be provided may be changed based on attribute information of an target object B, and the changed recommended location information may be stored with the attribute information of the target object B. Otherwise, a size of the recommended location information may be expanded or reduced and a location where the recommended location information is to be provided may be changed based on attribute information of an target object C, and the changed recommended location information may be stored with the attribute information of the target object C.

Figure 21:
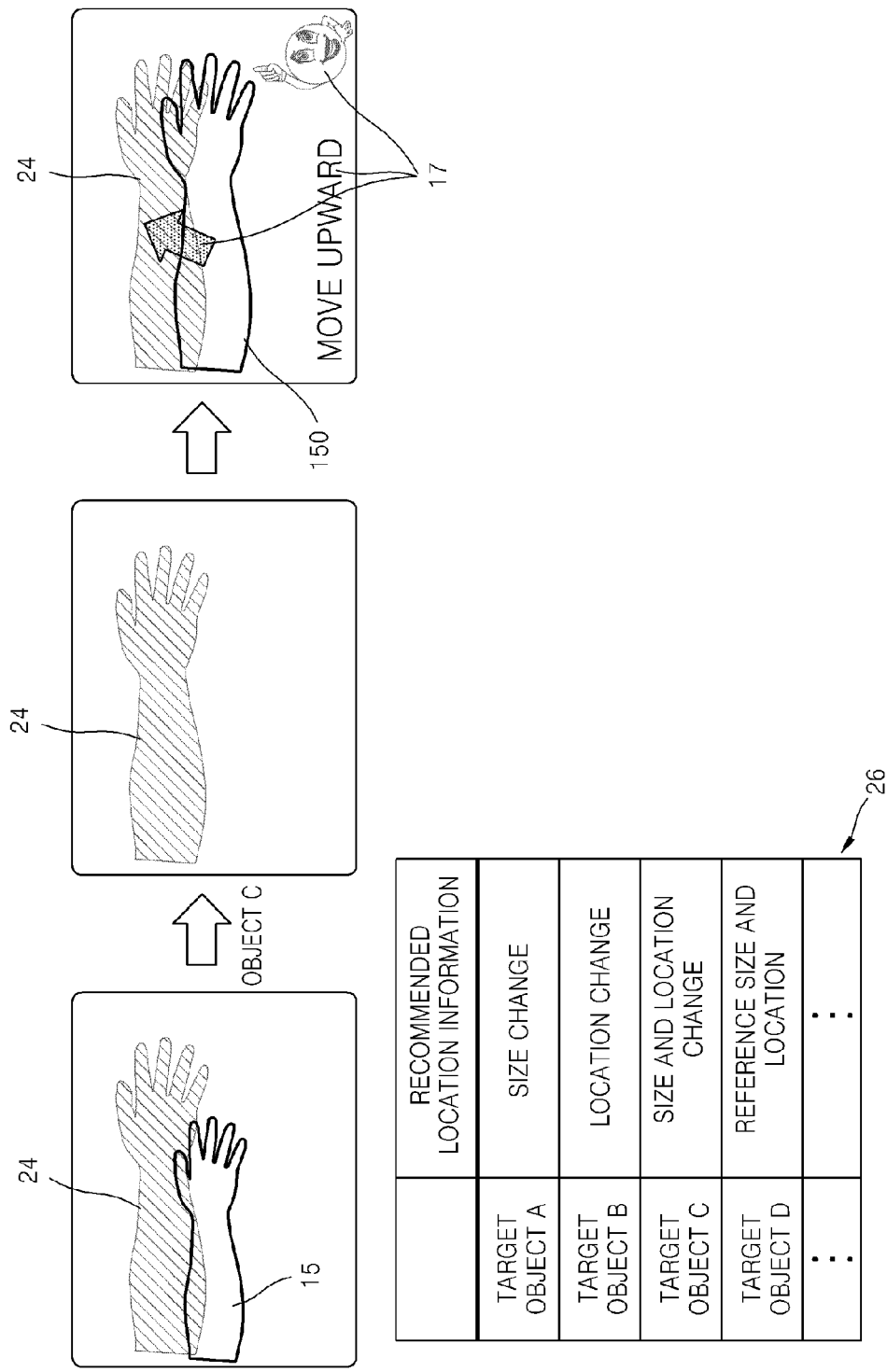
FIG. 21 is a diagram showing an example of using recommended location information, edited according to an embodiment.

FIG. 21 is a diagram showing an example of using edited recommended location information, according to an embodiment.

As described above with reference to FIG. 20, when the recommended location information that is edited (for example, changed and stored) is used when photographing the target object 150, a time for setting photographing environment with respect to the target object 150 may be reduced.

For example, when an arm of the target object 150 is to be photographed, a photographing portion of the target object 150 may be set as the arm. If the edited recommended location information is not used, the recommended location information 15, including the guide line, is acquired based on the contour line 12 that is obtained from the reference image 10 according to the photographing portion, and the recommended location information has to be independently adjusted with respect to each target object after reflecting the attribute information of the target object in the recommended location information 15. Therefore, when the edited recommended location information is used, the time for setting the photographing environment with respect to the target object 150 may be reduced.

For example, when an target object C is to be photographed, the information, such as the changed size and the location of the guide line representing the recommended location of the target object C, is stored in advance in a storage unit (not shown) as a table 26. Thus, according to the present embodiment, the information about the target object C is loaded from the storage unit (not shown) to provide the recommended location information 24 suitable for the target object C. Also, as shown in FIG. 21, at least one of the recommended location information 24 suitable for the target object C and the additional information 17 may be provided.

That is, at least one of the recommended location information that is edited by reflecting the properties of each target object and the additional information may be provided to the target object, and the time for setting the photographing environment may be reduced.

Figure 22:
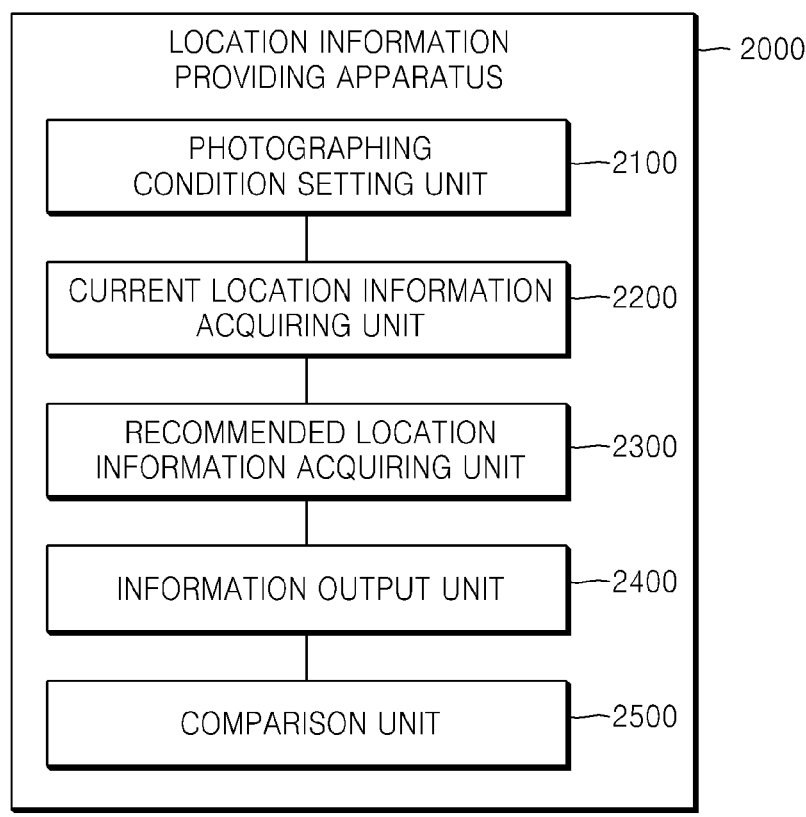
FIG. 22 is a diagram showing an apparatus for providing information regarding a location of a target object through a medical apparatus, according to an embodiment.

FIG. 22 is a diagram of an apparatus 200 for providing information regarding a location of an target object through a medical apparatus, according to an embodiment.

According to the present embodiment, the apparatus 2000 for providing information regarding the location of the target object through the medical apparatus may include a photographing condition setting unit 2100 for setting photographing conditions about the target object, a current location information acquiring unit 2200 for acquiring current location information of the target object, a recommended location information acquiring unit 2300 for obtaining recommended location information of the target object according to set photographing conditions, an information output unit 2400 outputting the acquired recommended location information, and a comparison unit 2500 for comparing the current location information with the recommended location information. Also, additional information about the current location of the target object may be output through the information output unit 2400 according to a comparison result of the comparison unit 2500.

The medical apparatus according to the present embodiment may include an X-ray apparatus.

The photographing condition according to the present embodiment may include a medical apparatus selection condition for selecting the medical apparatus, and a photograph selection condition for selecting a portion to be photographed.

In addition, the photographing condition according to the present embodiment may include a condition about at least one of the X-ray tube location, a collimation size, a location of the X-ray detector, and a resolution of the image.

Also, the photographing condition according to the present embodiment may be set based on the attribute information of the target object. The attribute of the target object may include age, gender, height, weight, body shape, a portion to be photographed, and medical history.

The current location information acquiring unit 2200 according to the present embodiment may include at least one camera. The camera according to the present embodiment may include a 2D single camera 120a, a 2D stereo camera 120b, and a 3D depth camera 120c.

The recommended location information 15 according to the present embodiment may include a predetermined line, a marker, or a composite image. The predetermined line may include a guide line. The marker may denote a marker of a shadow type that corresponds to the portion to be photographed. Also, the recommended location information may be provided as a composite image after being combined with an image showing a current posture of the target object.

Figure 23:
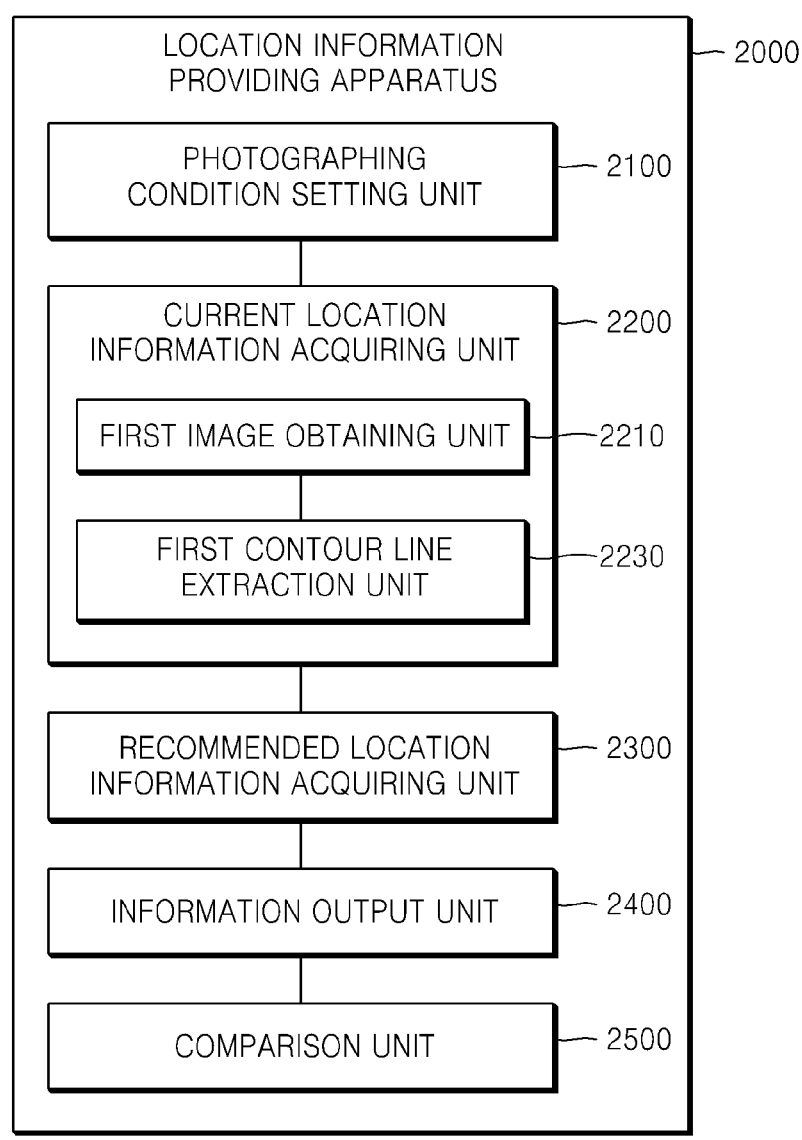
FIG. 23 is a diagram of an apparatus including a current location information obtaining unit of the apparatus, according to an embodiment.

FIG. 23 is a diagram showing the current location information acquiring unit 2200 of the apparatus 2000 including, according to an embodiment.

The current location information acquiring unit 2200 according to the present embodiment may include a first image obtaining unit 2210 for obtaining an image including an target object by using at least one camera under the photographing condition set by the photographing condition setting unit 2100, and a first contour line extraction unit 2230 for extracting a contour line of the target object from the acquired image. The current location information may include information about the contour line. That is, the current location information may include contour line information with respect to the current position (or location) of the target object.

The contour line of the current posture (or location) of the target object may be extracted by using a segmentation method used in a general image processing field, as described above. Also, the contour line of the current posture of the target object may be obtained by using a difference between depth information of the target object.

Figure 24:
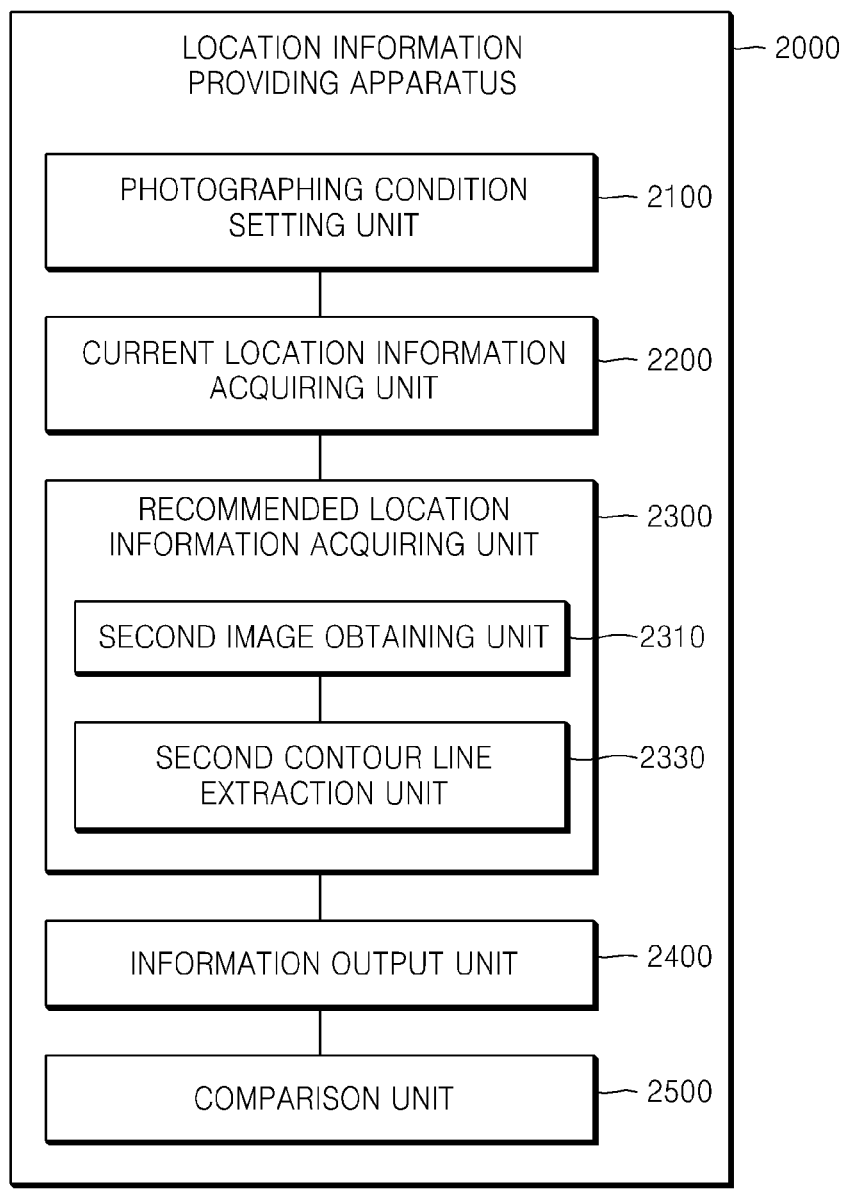
FIG. 24 is a diagram of an apparatus including a recommended location information obtaining unit of the apparatus, according to an embodiment.

FIG. 24 is a diagram showing the recommended location information acquiring unit 2300 of the apparatus 2000, according to an embodiment.

The recommended location acquiring unit 2300 according to the present embodiment may include a second image obtaining unit 2310 for obtaining a reference image related to the target object, and a second contour line extraction unit 2330 for extracting a contour line of a region included in the reference image and corresponding to the target object. The recommended location information may include information about the contour line of the region extracted from the reference image.

The reference image 10 of the target object according to the present embodiment is determined statistically according to portions of the target object and stored in advance in a database.

Also, the reference image 10 according to the present embodiment may be selected based on properties of the target object to be photographed from among images of a plurality of object bodies, which are stored in advance.

In addition, the reference image 10 according to the present embodiment may be an image having the highest clarity of the target object under the set photographing conditions. As described above, a clear image of the target object has to be obtained in order to perform an accurate diagnosis. Therefore, the reference image 10 according to the present embodiment may be an image having the highest clarity from among the images stored in advance.

According to the present embodiment, the reference image 10 may be acquired for the portion to be photographed. The contour line 12 of the region corresponding to the target object (or the portion to be photographed of the target object) may be extracted from the reference image 10. The recommended location information 15 with respect to the target object may be determined in advance by using the contour line 12.

For example, the recommended location information 15 may be determined by using at least one of a location or a size of the contour line 12 in the reference image 10. That is, a location for providing the recommended location information 15 may be determined to correspond to the location of the contour line 12 in the reference image 10. In addition, a size of the recommended location information 15 may be determined in consideration of a size (or area) rate of the contour line 12 with respect to a size (or entire area) of the reference image 10.

The information output unit 2400 according to the present embodiment may include a projector for projecting the recommended location information toward the target object. The information output unit 2400 may be located at a side of the X-ray source 100 or an X-ray detector 110.

For example, the recommended location information 15 may be directly projected toward the X-ray detector 110 from the projector 141 disposed at the side of the X-ray source 100, or may be projected directly onto the target object 150 located on the X-ray detector 110.

Also, the information output unit 2400 may further include a predetermined screen 142. For example, the screen 142 for displaying the image projected from the projector 141 located at the side of the X-ray detector 110 may be located on a fixing axis or a supporting axis of the X-ray source 100.

That is, since the projector 141 is located on the fixing axis or the supporting axis of the X-ray detector 110 and the screen 142 is located on the fixing axis of the supporting axis of the X-ray source 100, at least one of the recommended location information and the additional information may be provided to the target object via the projector 141 and the screen 142.

According to the present embodiment, the target object may correct his/her posture by using the at least one of the recommended location information and the additional information provided through the projector 141 and the screen 142. The user may determine whether to proceed with the photographing process fast and exactly.

Figure 25:
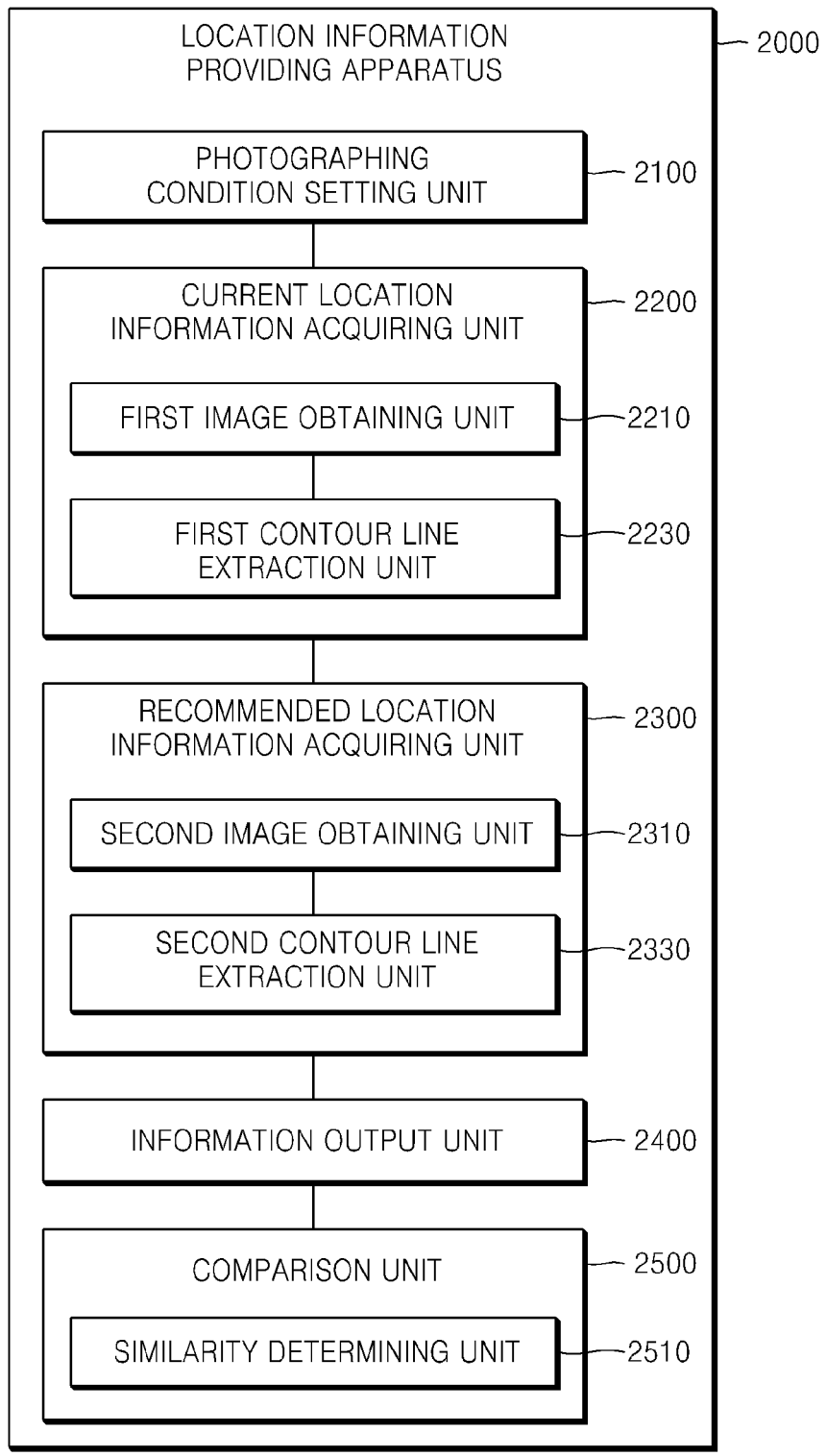
FIG. 25 is a diagram of a comparison unit of the apparatus, according to an embodiment.

FIG. 25 is a diagram showing a comparison unit 2500 of the apparatus 200, according to an embodiment.

The comparison unit 2500 according to the present embodiment may include a similarity determination unit 2510 for determining a similarity between the current location information and the recommended location information.

A contour line 13 from the current location of the target object is extracted, and it may be determined whether the posture of the target object is suitable for the recommended location based on a concordance rate between the contour line 13 and the recommended location information 15. According to the present embodiment, the similarity may be determined based on the concordance rate between the contour line 13 extracted from the current location of the target object and the recommended location information 15.

For example, if the contour line 13 of the target object and the recommended location information 15 do not overlap with each other, it may be determined that the contour line 13 of the target object and the recommended location information 15 are not similar to each other at all, and the target object 150 has to move so as to overlap with the recommended location information 15.

However, when the contour line 13 of the target object and the recommended location information 15 completely overlap with each other, it may be determined that locations of the contour line 13 of the target object and the recommended location information 15 are the same. For example, since the posture of the target object 150 is suitable for the recommended location information 15, it is necessary to maintain the posture during the photographing process.

According to the present embodiment, the additional information about the current location of the target object may be output through the information output unit 2400 according to a similarity comparison result between the current location information expressed by the contour line 13 of the target object and the recommended location information. The additional information may include at least one of information regarding the location correction of the target object, and information representing the similarity.

The additional information according to the present embodiment may be output in at least one format of the text, sound, and an image.

When the posture of the target object is suitable for the recommended location information, a predetermined message may be output as the additional information 17. For example, a message such as "exact" may be output as the information relating to the location correction of the target object. The output of the additional information may include displaying the message on a device having a display function.

Also, when the posture of the target object is suitable for the recommended location information, an emoticon, such as a smile character having the biggest smile, may be output as the additional information 17. That is, as the target object and the recommended location information gradually overlap with each other, the smile character may be changed to show a bigger smile.

Similarly, a predetermined image, including an icon that is changed when the target object and the recommended location information gradually overlap with each other, may be output as the additional information 17. For example, when the target object and the recommended location information do not match, an X icon may be output, and when the object and the recommended location information match, an O icon (or image) may be output.

The similarity (or concordance rate) between the target object and the recommended location information may be represented by numbers. For example, when the target object and the recommended location information do not overlap with each other, letters or numbers such as "similarity 0%" may be output as the additional information. When the target object and the recommended location information completely overlap with each other, letters or numbers such as "concordance rate 100%" may be output as the additional information.

According to the present embodiment, if the target object and the recommended location information do not overlap with each other, information related to the location correction may be output as the additional information. For example, a message, such as "move your right arm upward", may be provided as the information for correcting the location. Also, when the target object moves and overlaps with the recommended location information, a message, such as "exact, please do not move", may be output as the additional information.

When the target object moves and overlaps with the recommended location information, a change in a color or texture of the recommended location information may be output as the additional information. For example, as described above, when the target object overlaps with the recommended location information after moving, the recommended location information may be changed from a diagonal pattern to a check pattern.

According to the present embodiment, if the target object does not overlap with the recommended location information, information regarding to the correction of the location may be output as the additional information. For example, a direction (for example, at least one of the direction and angle) in which the target object has to move in order to overlap with the recommended location information or a distance (for example, a few cm) that the target object has to move may be provided as the information related to the correction of the location by using an arrow or numbers.

Otherwise, the direction or the distance that the target object has to move may be expressed by a predetermined image, such as a character. The image may include an animation image or a moving picture. In addition, when the target object overlaps with the recommended location information, an image having the biggest smile may be output as the additional information.

Also, the additional information may be provided to the target object as sound, such as a voice through a speaker. For example, the additional information, such as the message "move your right arm upward" or "exact, please do not move" may be provided to the target object as the voice through the speaker.

Figure 26:
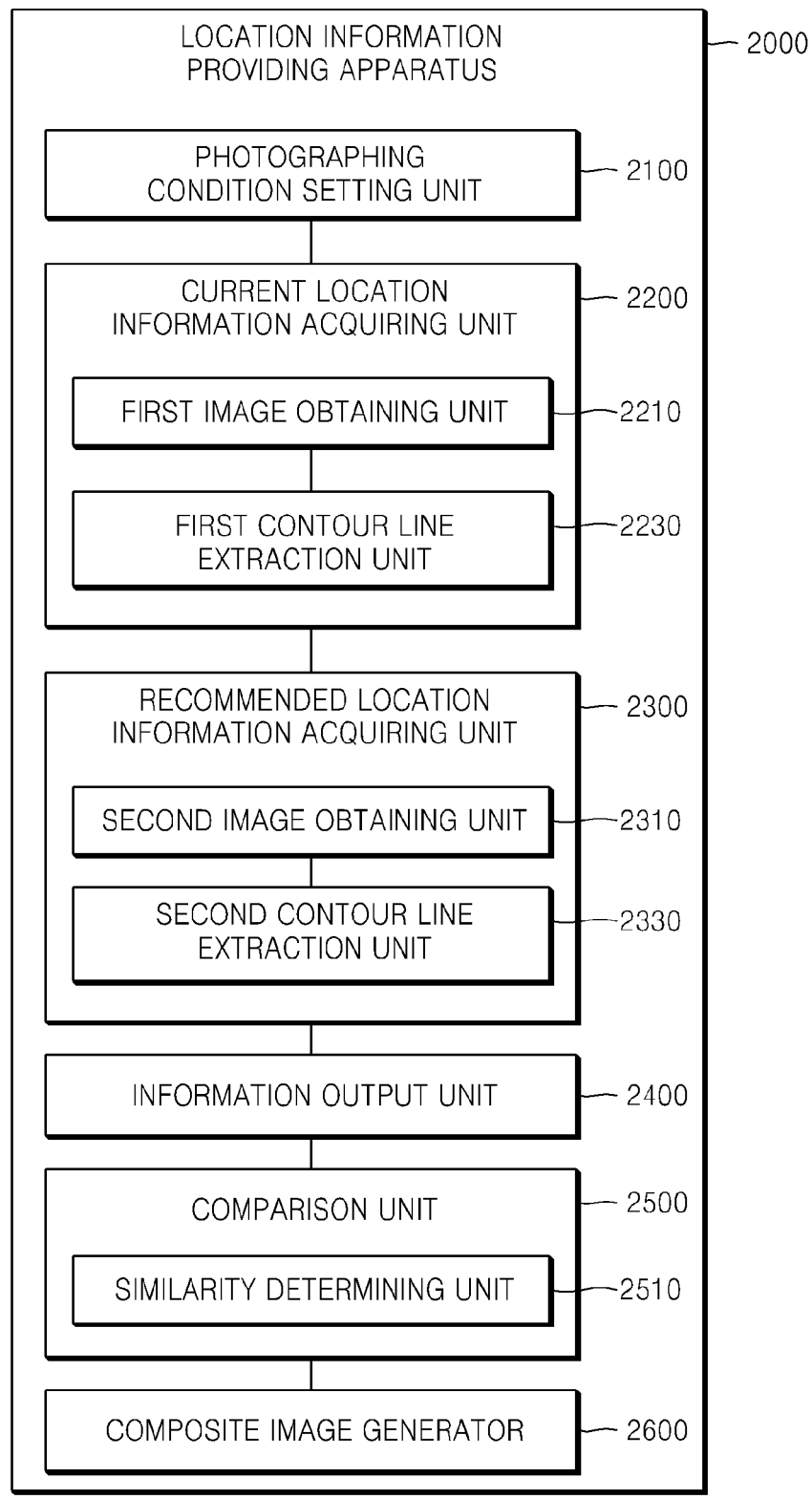
FIG. 26 is a diagram of an exemplary combination image generator of the apparatus, according to an embodiment.

FIG. 26 is a diagram showing a composite image generator 2600 of the apparatus 2000, according to an embodiment.

The apparatus 2000 of the present embodiment may further include the composite image generator 2600 for generating a composite image by overlapping a contour line of a region extracted from a second image with a first image.

The information output unit 2400 may output the composite image generated by the composite image generator 2600, for example, may display the composite image.

Also, as described above, the information output unit 2400 may include a device having a display function, which may be located at least at a side of the X-ray source 100 or the X-ray detector 110.

The device having the display function according to the present embodiment may include at least one of the LCD panel 131 or 132, the projector 141, and a head-mounted display (HMD) 180. The projector 141 may further include the image transfer unit 143.

As described above with reference to FIG. 18, the image transfer unit 143 may include a reflector, such as at least one mirror. The image transfer unit 143 may move in a predetermined direction or angle.

The recommended location information according to the present embodiment may be provided via the wearable device 180. The wearable device 180 may include augmented reality glasses or an HMD, as described above with reference to FIG. 19A.

For example, the target object wearing the wearable device 180 may receive at least one of the recommended location information 15 and the additional information 17 via the wearable device 180.

The recommended location information 15 according to the present embodiment may be changed according to the attribute information of the target object. In addition, the recommended location information 15 that is variable may be stored to correspond to the attribute information of the target object.

For example, the recommended location information 15 that is obtained based on the contour line 12 corresponding to the target object from the reference image 10 may be changed with respect to each target object according to the attribute information 22 of the target object.

That is, the recommended location information 15 with respect to each target object may have a bigger or smaller size than that of the recommended location information 15 before being changed, or may be provided at the location moving from the original recommended location information 15 in at least one of the upper, lower, left, right, and diagonal directions. In other words, at least one of the size and the location of the recommended location information may be changed according to the attribute information of the target object. For example, with respect to the target object having a greater volume and less height than those of a reference target object, the guide line representing the recommended location may be expanded and the recommended location information may be provided at a lower location.

Also, the recommended location information that is variable according to the present embodiment may be stored as the table 26 corresponding to the attribute information of the target object, as shown in FIG. 20. In addition, the recommended location information may be stored as the table 26 corresponding to an identifier (for example, an ID) of the target object. The identifier of the target object may include an exclusive code consisting of letters or numbers. The attributes of the target object may include age, gender, height, weight, body shape, a portion to be photographed, and medical history, as described above.

According to the present embodiment, the time for setting the photographing environment with respect to the object may be reduced by using the recommended location information that is stored to correspond to the attribute information of the target object.

For example, as shown in FIG. 20, when an target object B is to be photographed by using the recommended location information that is edited as the table 26, the location of the guide line representing the recommended location of the target object B may be automatically provided after being stored in the table 26 in a storage unit (not shown). That is, information about the target object B may be loaded from the storage unit (not shown), and then, the recommended location information may be provided to the target object B. Also, at least one of the recommended location information suitable for the target object B and the additional information may be provided.

According to the embodiments, when photographing an target object by using a medical apparatus, information about a recommended location of the target object (patient) is provided to the patient or the user of the medical apparatus, and thus, interaction and communication between the patient and the user of the medical apparatus may be supported. For example, if the patient is a woman, a child, or a foreigner, difficulties in communication between the patient and the medical expert may be reduced.

The above description about the method may be applied to the apparatus according to the embodiment. Therefore, the same descriptions as those of the above described method are not provided here.

In addition, other embodiments can also be implemented through computer-readable code/instructions in/on a medium, e.g., a computer-readable medium, to control at least one processing element to implement any above described embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to one or more embodiments. The media may also be a distributed network, so that the computer-readable code is stored/transferred and executed in a distributed fashion. Furthermore, the processing element could include a processor or a computer processor, and processing elements may be distributed and/or included in a single device.

While the embodiments have been particularly shown and described with reference to exemplary embodiments thereof, it will be understood by those of ordinary skill in the art that various changes in form and details may be made therein without departing from the spirit and scope of the embodiments as defined by the following claims.

What is claimed is:

1. A method comprising:
    performing, by at least one processor, operations including:
        acquiring an image, using a camera, of a target object at a current location;
        acquiring a recommended location for the target object;
        comparing the acquired image of the current location of the target object to the acquired recommended location for the target object;
        determining adjustment information for the acquired image of the current location of the target object relative to the acquired recommended location of the target object, based on the comparing; and
        generating a composite image including the acquired image of the target object at the current location, an outline of the target object at the recommended location, and the determined adjustment information on the target object to provide a visual guide to move the target object from the current location to the recommended location,
    wherein the determining adjustment information comprises:
        extracting a contour line of the image of the current location from the acquired image of the target object; and
        determining a similarity based on an overlapping degree between the contour line and the recommended location of the target object.

2. The method of claim 1, wherein the method is executed using an X-ray apparatus, and the method further comprises:
    setting photographing conditions about the target object, wherein the photographing conditions comprise conditions about at least one of a location of an X-ray tube, a size of a collimation, a location of an X-ray detector, and a resolution of an image.

3. The method of claim 2, wherein the photographing conditions are set based on attribute information of the target object.

4. The method of claim 1, wherein the method further comprises:
acquiring a reference image related to the target object, and
extracting a contour line of a region included in the reference image and that corresponds to the target object,
wherein the recommended location comprises information about the contour line.

5. The method of claim 4, wherein the acquired reference image is an image among a plurality of stored images that has a maximum clarity of a portion of the target object, which is to be photographed, under photographing conditions that have been set.

6. The method of claim 1, wherein the generating the composite image comprises generating at least one of information regarding a correction of the location of the target object and information representing the similarity between the acquired current location and the acquired recommended location.

7. The method of claim 6, wherein the adjustment information may be output in at least one of text, sound, and an output image.

8. The method of claim 4, wherein the generating the composite image further comprises:
generating the composite image by overlapping the acquired image of the target object with a contour line of a region included in the reference image, and
displaying the generated composite image.

9. The method of claim 8, wherein the composite image is displayed on a display unit that is provided on at least a side of an X-ray source and an X-ray detector.

10. The method of claim 9, wherein the display unit comprises at least one of a liquid crystal display (LCD) panel, a projector, and a head-mounted display (HMD), and the projector may further comprise an image transfer unit.

11. The method of claim 1, the method further comprising outputting at least one of information for correcting the current location of the target object and information for representing the similarity.

12. The method of claim 11, wherein the adjustment information may be output in at least one of text, sound, and an output image.

13. The method of claim 1, wherein the recommended location is variable depending on attribute information of the target object, and the recommended location that is variable is stored to correspond to the attribute information of the target object.

14. A non-transitory computer-readable recording medium having embodied thereon a program for executing the method according to claim 1.

15. An apparatus comprising:
at least one memory configured to store instructions;
at least one processor configured to execute the stored instructions to implement a method comprising:
acquiring an image, using a camera, of a target object at a current location;
acquiring a recommended location for the target object;
comparing the acquired image of the current location of the target object to the acquired recommended location for the target object;
determining adjustment information for the acquired image of the current location of the target object relative to the acquired recommended location of the target object, based on the comparing; and
generating a composite image including the acquired image of the target object at the current location, an outline of the target object at the recommended location, and the determined adjustment information on the target object to provide a visual guide to move the target object from the current location to the recommended location,
wherein the at least one processor is further configured to extract a contour line of the image of the current location from the acquired image of the target object and determine a similarity based on an overlapping degree between the contour line and the recommended location of the target object.

16. The apparatus of claim 15, wherein the apparatus comprises an X-ray apparatus, and the at least one processor is further configured to set photographing conditions about the target object, wherein the photographing conditions comprise conditions about at least one of a location of an X-ray tube, a size of the collimation, a location of an X-ray detector, and a resolution of an image.

17. The apparatus of claim 16, wherein the photographing conditions are set based on attribute information of the target object.

18. The apparatus of claim 15, wherein the at least one processor is further configured to execute the instructions stored in the at least one memory to cause the following to be performed:
acquiring a reference image related to the target object, and
extracting a contour line of a region included in the reference image and that corresponds to the target object,
wherein the recommended location comprises information about the contour line of the region.

19. The apparatus of claim 18, wherein the acquired reference image is an image among a plurality of stored images that has a maximum clarity of a portion of the target object, which is to be photographed, under photographing conditions that have been set.

20. The apparatus of claim 15, wherein the adjustment information comprises at least one of information regarding a correction of the location of the target object and information representing the similarity between the acquired current location and the acquired recommended location.

21. The apparatus of claim 20, wherein the adjustment information may be output in at least one of text, sound, and an output image.

22. The apparatus of claim 18, wherein the at least one processor further executes the instruction to generate the composite image by overlapping the image of the target object with the contour line of the region, and
wherein the apparatus further includes a screen to display the generated composite image.

23. The apparatus of claim 22, wherein the screen is provided on at least a side of an X-ray source and an X-ray detector.

* * * * *